US010973699B2

(12) United States Patent
Schneider et al.

(10) Patent No.: US 10,973,699 B2
(45) Date of Patent: Apr. 13, 2021

(54) METHODS AND APPARATUSES FOR MAKING ELASTOMERIC LAMINATES WITH ELASTIC STRANDS UNWOUND FROM BEAMS

(71) Applicant: The Procter & Gamble Company, Cincinnati, OH (US)

(72) Inventors: Uwe Schneider, Cincinnati, OH (US); Joseph Allen Eckstein, Sunman, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 32 days.

(21) Appl. No.: 15/831,448

(22) Filed: Dec. 5, 2017

(65) Prior Publication Data

US 2018/0168878 A1 Jun. 21, 2018

Related U.S. Application Data

(60) Provisional application No. 62/436,589, filed on Dec. 20, 2016, provisional application No. 62/483,965, (Continued)

(51) Int. Cl.
*A61F 13/15* (2006.01)
*A61F 13/49* (2006.01)
(Continued)

(52) U.S. Cl.
CPC .... *A61F 13/15593* (2013.01); *A61F 13/4902* (2013.01); *A61F 13/49061* (2013.01);
(Continued)

(58) Field of Classification Search
CPC .......... A61F 13/49061; A61F 13/51464; A61F 2013/15447; A61F 2013/51322;
(Continued)

(56) References Cited

U.S. PATENT DOCUMENTS 3,113,225 A 12/1963 Kleesattel et al.
3,434,189 A 3/1969 Buck et al.
(Continued)

FOREIGN PATENT DOCUMENTS

CA 2158790 3/1996
CN 1276196 A 6/1999
(Continued)

OTHER PUBLICATIONS

PCT International Search Report, dated Mar. 21, 2018, 13 pages.
(Continued)

*Primary Examiner* — Vishal I Patel
(74) *Attorney, Agent, or Firm* — Charles R. Matson

(57) ABSTRACT

The present disclosure relates to methods for assembling elastomeric laminates, wherein elastic material may be stretched and joined with either or both first and second substrates. A first beam is rotated to unwind a first plurality of elastic strands from the first beam in the machine direction. The first plurality of elastic strands are positioned between the first substrate and the second substrate to form the elastomeric laminate. Before the first plurality of elastic strands are completely unwound from the first beam, a second beam is rotated to unwind the second plurality of elastic strands from the second beam. Subsequently, the advancement of the first plurality of elastic strands from the first beam is discontinued. Thus, the elastomeric laminate assembly process may continue uninterrupted while switching from an initially utilized elastic material drawn from the first beam to a subsequently utilized elastic material drawn from the second beam.

14 Claims, 20 Drawing Sheets

Related U.S. Application Data filed on Apr. 11, 2017, provisional application No. 62/553,149, filed on Sep. 1, 2017, provisional application No. 62/553,171, filed on Sep. 1, 2017, provisional application No. 62/581,278, filed on Nov. 3, 2017, provisional application No. 62/553,538, filed on Sep. 1, 2017.

(51) Int. Cl.

| | | |
|---|---|---|
| B32B 27/12 | (2006.01) | |
| D01D 5/08 | (2006.01) | |
| B29C 65/08 | (2006.01) | |
| B29C 65/48 | (2006.01) | |
| B29L 31/48 | (2006.01) | |
| B05C 1/08 | (2006.01) | |
| B32B 37/14 | (2006.01) | |
| B65H 39/16 | (2006.01) | |
| B65H 51/30 | (2006.01) | |
| B29C 65/00 | (2006.01) | |
| B29C 65/74 | (2006.01) | |
| B29K 701/12 | (2006.01) | |
| A61F 13/53 | (2006.01) | |
| A61F 13/64 | (2006.01) | |
| A61F 13/84 | (2006.01) | |
| B32B 5/04 | (2006.01) | |
| B32B 37/00 | (2006.01) | |
| B32B 37/12 | (2006.01) | |
| D04H 3/12 | (2006.01) | |
| A61F 13/56 | (2006.01) | |
| B32B 37/22 | (2006.01) | |
| A61F 13/513 | (2006.01) | |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *D01D 5/08* (2013.01); *D04H 3/12* (2013.01)

(58) Field of Classification Search
CPC .......... A61F 13/15739; A61F 13/49019; A61F 13/493; A61F 2013/15918; A61F 13/15764; A61F 13/49014; A61F 13/49015; A61F 13/15699; A61F 13/15; A61F 2013/15959; A61F 13/64; A61F 2013/15292; A61F 13/49011; A61F 2013/49092; A61F 2013/8497; A61F 2013/1591; A61F 13/15593; A61F 2013/15552; A61F 2013/49022; A61F 13/49012; A61F 13/51478; A61F 13/15601; A61F 13/5622; A61F 13/15585; A61F 13/496; A61F 13/491; A61F 13/4902; A61F 2013/49074; A61F 2013/49093; A61F 2013/49025; A61F 13/53; A61F 2013/15869; A61F 13/55115; A61F 2013/15373; A61F 2013/530343; A61F 13/15203; A61F 2013/49026; A61F 13/49017; A61F 2013/15406; A61F 2013/49031; B29C 65/74; B29C 66/01; B29C 66/344; B29C 66/8141; B29C 65/48; B29C 65/086; B29C 65/08; B29C 66/83411; B32B 5/04; B32B 2307/726; B32B 2305/20; B32B 37/0053; B32B 37/22; B32B 2307/51; B32B 37/12; B32B 7/12; B32B 2555/02; B32B 37/144; B32B 5/022; B32B 27/12; D04H 3/005; D04H 3/12; D01D 5/08; B29K 2995/0092; B29K 2701/12; B29K 2995/0046; B29K 2995/0093; D01F 6/04; D01F 6/62; B29L 2031/4878; D02G 3/32; C08J 2300/26; B65H 39/16; B65H 51/30; B05C 1/0808

See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long et al. |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen et al. |
| 4,657,539 A | 4/1987 | Hasse |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen et al. |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |

(56) References Cited

U.S. PATENT DOCUMENTS

| | | | |
|---|---|---|---|
| 5,334,289 A | 8/1994 | Trokhan et al. | |
| 5,342,341 A | 8/1994 | Igaue et al. | |
| 5,360,420 A | 11/1994 | Cook et al. | |
| 5,393,360 A | 2/1995 | Bridges et al. | |
| 5,413,849 A | 5/1995 | Austin et al. | |
| 5,514,523 A | 5/1996 | Trokhan et al. | |
| 5,531,729 A | 7/1996 | Coles et al. | |
| 5,558,658 A | 9/1996 | Menard et al. | |
| 5,562,646 A | 10/1996 | Goldman et al. | |
| 5,569,234 A | 10/1996 | Buell et al. | |
| 5,575,874 A | 11/1996 | Griesbach, III et al. | |
| 5,599,335 A | 2/1997 | Goldman et al. | |
| 5,599,420 A | 2/1997 | Yeo et al. | |
| 5,628,097 A | 5/1997 | Benson et al. | |
| 5,643,588 A | 7/1997 | Roe et al. | |
| 5,643,653 A | 7/1997 | Griesbach, III et al. | |
| 5,669,894 A | 9/1997 | Goldman et al. | |
| 5,674,216 A | 10/1997 | Buell et al. | |
| 5,702,551 A | 12/1997 | Huber et al. | |
| 5,775,380 A | 7/1998 | Roelstraete et al. | |
| 5,827,259 A | 10/1998 | Laux et al. | |
| 5,858,504 A | 1/1999 | Steven | |
| 5,887,322 A * | 3/1999 | Hartzheim | B65H 69/02 242/556.1 |
| 5,895,623 A | 4/1999 | Trokhan et al. | |
| 5,897,545 A | 4/1999 | Kline et al. | |
| 5,916,661 A | 6/1999 | Benson et al. | |
| 5,957,908 A | 9/1999 | Kline et al. | |
| 5,968,025 A | 10/1999 | Roe et al. | |
| 5,993,433 A | 11/1999 | St Louis et al. | |
| 5,997,521 A | 12/1999 | Robles et al. | |
| 6,036,796 A | 3/2000 | Halbert et al. | |
| 6,043,168 A | 3/2000 | Colman et al. | |
| 6,107,537 A | 8/2000 | Elder et al. | |
| 6,107,539 A | 8/2000 | Palumbo et al. | |
| 6,118,041 A | 9/2000 | Roe et al. | |
| 6,120,487 A | 9/2000 | Ashton | |
| 6,120,489 A | 9/2000 | Johnson et al. | |
| 6,139,941 A | 10/2000 | Jankevics et al. | |
| 6,153,209 A | 11/2000 | Vega et al. | |
| 6,248,195 B1 | 6/2001 | Schmitz | |
| 6,248,197 B1 | 6/2001 | Nakanishi et al. | |
| 6,291,039 B1 | 9/2001 | Combe et al. | |
| 6,319,239 B1 | 11/2001 | Daniels et al. | |
| 6,361,638 B2 | 3/2002 | Takai et al. | |
| 6,383,431 B1 | 5/2002 | Dobrin et al. | |
| 6,395,957 B1 | 5/2002 | Chen et al. | |
| 6,410,129 B2 | 6/2002 | Zhang et al. | |
| 6,426,444 B2 | 7/2002 | Roe et al. | |
| 6,475,600 B1 | 11/2002 | Morman et al. | |
| 6,478,785 B1 | 11/2002 | Ashton et al. | |
| 6,482,191 B1 | 11/2002 | Roe et al. | |
| 6,508,641 B1 | 1/2003 | Kubik | |
| 6,545,197 B1 | 4/2003 | Muller et al. | |
| 6,554,815 B1 | 4/2003 | Umebayashi | |
| 6,586,652 B1 | 7/2003 | Roe et al. | |
| 6,617,016 B2 | 9/2003 | Zhang et al. | |
| 6,627,787 B1 | 9/2003 | Roe et al. | |
| 6,632,504 B1 | 10/2003 | Gillespie et al. | |
| 6,645,330 B2 | 11/2003 | Pargass et al. | |
| 6,673,418 B1 | 1/2004 | DeOlivera et al. | |
| 6,676,054 B2 | 1/2004 | Heaney et al. | |
| 6,702,798 B2 | 3/2004 | Christoffel et al. | |
| 6,790,798 B1 | 9/2004 | Suzuki et al. | |
| 6,821,301 B2 | 11/2004 | Azuse et al. | |
| 6,825,393 B2 | 11/2004 | Roe et al. | |
| 6,861,571 B1 | 3/2005 | Roe et al. | |
| 7,008,685 B2 | 3/2006 | Groitzsch et al. | |
| 7,118,558 B2 | 10/2006 | Wu et al. | |
| 7,465,367 B2 | 12/2008 | Day | |
| 7,569,039 B2 | 8/2009 | Matsuda et al. | |
| 7,582,348 B2 | 9/2009 | Ando et al. | |
| 7,642,398 B2 | 1/2010 | Järpenberg et al. | |
| 7,708,849 B2 | 5/2010 | McCabe | |
| 7,777,094 B2 | 8/2010 | Mori et al. | |
| 7,861,756 B2 | 1/2011 | Jenquin et al. | |
| 7,878,447 B2 | 2/2011 | Hartzheim | |
| 7,901,393 B2 | 3/2011 | Matsuda et al. | |
| 7,905,446 B2 | 3/2011 | Hartzheim | |
| 7,954,213 B2 | 6/2011 | Mizutani et al. | |
| 8,093,161 B2 | 1/2012 | Bansal et al. | |
| 8,143,177 B2 | 3/2012 | Noda et al. | |
| 8,186,296 B2 | 5/2012 | Brown et al. | |
| 8,226,625 B2 | 7/2012 | Turner et al. | |
| 8,308,706 B2 | 11/2012 | Fukae | |
| 8,377,554 B2 | 2/2013 | Martin et al. | |
| 8,388,594 B2 | 3/2013 | Turner et al. | |
| 8,440,043 B1 | 5/2013 | Schneider et al. | |
| 8,585,666 B2 | 11/2013 | Weisman et al. | |
| 8,647,319 B2 | 2/2014 | Een et al. | |
| 8,729,332 B2 | 5/2014 | Takahashi et al. | |
| 8,778,127 B2 | 7/2014 | Schneider et al. | |
| 8,853,108 B2 | 10/2014 | Ahoniemi et al. | |
| 8,906,275 B2 | 12/2014 | Davis et al. | |
| 8,939,957 B2 | 1/2015 | Raycheck et al. | |
| 9,005,392 B2 | 4/2015 | Schneider et al. | |
| 9,039,855 B2 | 5/2015 | Schneider et al. | |
| 9,050,213 B2 | 6/2015 | LaVon et al. | |
| 9,156,648 B2 | 10/2015 | Yamamoto | |
| 9,168,182 B2 | 10/2015 | Hargett et al. | |
| 9,198,804 B2 | 12/2015 | Nakamura et al. | |
| 9,226,861 B2 | 1/2016 | LaVon et al. | |
| 9,248,054 B2 | 2/2016 | Brown et al. | |
| 9,265,672 B2 | 2/2016 | Brown et al. | |
| 9,295,590 B2 | 3/2016 | Brown et al. | |
| 9,440,043 B2 | 9/2016 | Schneider et al. | |
| 9,453,303 B2 | 9/2016 | Aberg et al. | |
| 9,539,735 B2 | 1/2017 | Ferguson et al. | |
| 9,732,454 B2 | 8/2017 | Davis et al. | |
| 9,758,339 B2 | 9/2017 | Yanez, Jr. et al. | |
| 9,795,520 B2 | 10/2017 | Kaneko et al. | |
| 9,877,876 B2 | 1/2018 | Huang et al. | |
| 10,190,244 B2 | 1/2019 | Ashraf et al. | |
| 10,596,045 B2 | 3/2020 | Koshijima et al. | |
| 10,792,194 B2 | 10/2020 | Hohm et al. | |
| 2001/0030014 A1 | 10/2001 | Kwok | |
| 2002/0026660 A1 | 3/2002 | Goda | |
| 2002/0046802 A1 | 4/2002 | Tachibana et al. | |
| 2002/0072723 A1 | 6/2002 | Ronn et al. | |
| 2002/0099347 A1 | 7/2002 | Chen et al. | |
| 2002/0103469 A1 | 8/2002 | Chen et al. | |
| 2002/0134067 A1 | 9/2002 | Heaney et al. | |
| 2002/0153271 A1 | 10/2002 | McManus et al. | |
| 2002/0177829 A1 | 11/2002 | Fell et al. | |
| 2003/0044585 A1 | 3/2003 | Taylor et al. | |
| 2003/0070780 A1 | 4/2003 | Chen et al. | |
| 2003/0087056 A1 | 5/2003 | Ducker et al. | |
| 2003/0093045 A1 | 5/2003 | Erdman | |
| 2003/0119404 A1 | 6/2003 | Belau et al. | |
| 2003/0125687 A1 | 7/2003 | Gubernick et al. | |
| 2003/0144643 A1 | 7/2003 | Järpenberg et al. | |
| 2003/0203162 A1 | 10/2003 | Christopher et al. | |
| 2003/0233082 A1 | 12/2003 | Kline et al. | |
| 2004/0006323 A1 | 1/2004 | Hall et al. | |
| 2004/0030317 A1 | 2/2004 | Torigoshi | |
| 2004/0059309 A1 | 3/2004 | Nortman | |
| 2004/0097895 A1 | 5/2004 | Busam et al. | |
| 2004/0127881 A1 | 7/2004 | Stevens et al. | |
| 2004/0133180 A1 | 7/2004 | Mori et al. | |
| 2004/0158212 A1 | 8/2004 | Ponomarenko et al. | |
| 2004/0158217 A1 | 8/2004 | Wu et al. | |
| 2004/0219854 A1 * | 11/2004 | Groitzsch | A61F 13/622 442/328 |
| 2004/0230171 A1 | 11/2004 | Ando et al. | |
| 2005/0013975 A1 | 1/2005 | Brock et al. | |
| 2005/0107764 A1 | 5/2005 | Matsuda et al. | |
| 2005/0148971 A1 | 7/2005 | Kuroda et al. | |
| 2005/0230037 A1 | 10/2005 | Jenquin et al. | |
| 2005/0244640 A1 | 11/2005 | Riswick et al. | |
| 2005/0267431 A1 | 12/2005 | Sasaki et al. | |
| 2006/0047260 A1 | 3/2006 | Ashton et al. | |
| 2006/0069373 A1 | 3/2006 | Schlinz et al. | |
| 2006/0087053 A1 | 4/2006 | O'Donnell et al. | |
| 2006/0105075 A1 | 5/2006 | Otsubo | |

(56) References Cited

U.S. PATENT DOCUMENTS

| | | |
|---|---|---|
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba et al. |
| 2008/0287897 A1 | 11/2008 | Guzman et al. |
| 2009/0204093 A1 | 8/2009 | Vasic et al. |
| 2009/0312730 A1 | 12/2009 | LaVon et al. |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1 | 3/2010 | Hayase et al. |
| 2010/0248575 A1 | 9/2010 | Malz |
| 2010/0307668 A1 | 12/2010 | Lange et al. |
| 2011/0092943 A1 | 4/2011 | Bishop et al. |
| 2011/0118689 A1 | 5/2011 | Een et al. |
| 2011/0120897 A1 | 5/2011 | Takahashi |
| 2011/0250378 A1 | 10/2011 | Eaton et al. |
| 2012/0004633 A1 | 1/2012 | Marcelo et al. |
| 2012/0061015 A1 | 3/2012 | LaVon et al. |
| 2012/0061016 A1 | 3/2012 | LaVon et al. |
| 2012/0071852 A1 | 3/2012 | Tsang et al. |
| 2012/0095429 A1 | 4/2012 | Kobayashi et al. |
| 2012/0271267 A1 | 10/2012 | Love et al. |
| 2012/0277713 A1 | 11/2012 | Raycheck et al. |
| 2012/0323206 A1 | 12/2012 | McMorrow et al. |
| 2013/0032656 A1 | 2/2013 | Yamamoto et al. |
| 2013/0072887 A1 | 3/2013 | LaVon et al. |
| 2013/0112584 A1 | 5/2013 | Gaspari et al. |
| 2013/0139960 A1 | 6/2013 | Maruyama et al. |
| 2013/0171421 A1 | 7/2013 | Weisman et al. |
| 2013/0199696 A1 | 8/2013 | Schneider et al. |
| 2013/0199707 A1* | 8/2013 | Schneider ......... A61F 13/15593 156/164 |
| 2013/0211356 A1 | 8/2013 | Nishikawa et al. |
| 2013/0211363 A1 | 8/2013 | Lavon et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0261589 A1 | 10/2013 | Fujkawa et al. |
| 2013/0306226 A1 | 11/2013 | Zink et al. |
| 2014/0000794 A1 | 1/2014 | Hamilton et al. |
| 2014/0005621 A1 | 1/2014 | Roe et al. |
| 2014/0018759 A1 | 1/2014 | Jayasinghe et al. |
| 2014/0041797 A1 | 2/2014 | Schneider |
| 2014/0107605 A1 | 4/2014 | Schroer, Jr. et al. |
| 2014/0127460 A1 | 5/2014 | Xu et al. |
| 2014/0136893 A1 | 5/2014 | Xie et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1 | 9/2014 | Wang et al. |
| 2014/0276517 A1 | 9/2014 | Chester et al. |
| 2014/0288521 A1 | 9/2014 | Wade et al. |
| 2014/0296815 A1 | 10/2014 | Takken et al. |
| 2014/0302286 A1 | 10/2014 | Okuda et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck et al. |
| 2015/0136893 A1 | 5/2015 | Koskol |
| 2015/0164708 A1 | 6/2015 | Hashimoto et al. |
| 2015/0167207 A1 | 6/2015 | Bongartz et al. |
| 2015/0173967 A1 | 6/2015 | Kreuzer et al. |
| 2015/0230995 A1 | 8/2015 | Kaneko et al. |
| 2015/0245958 A1 | 9/2015 | Chmielewski et al. |
| 2015/0257941 A1 | 9/2015 | Eckstein et al. |
| 2015/0282999 A1 | 10/2015 | Arizti et al. |
| 2015/0320612 A1 | 11/2015 | Seitz et al. |
| 2015/0320613 A1 | 11/2015 | Seitz et al. |
| 2015/0320619 A1 | 11/2015 | Seitz et al. |
| 2015/0320620 A1 | 11/2015 | Seitz et al. |
| 2015/0320622 A1 | 11/2015 | Seitz et al. |
| 2015/0328056 A1 | 11/2015 | Een et al. |
| 2015/0351972 A1 | 12/2015 | Bing-Wo |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0270977 A1 | 9/2016 | Surushi et al. |
| 2016/0331600 A1 | 11/2016 | Polidori et al. |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0281417 A1 | 10/2017 | Ishikawa |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1 | 5/2018 | Koshijima et al. |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1 | 6/2018 | Zink, II et al. |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | La Von et al. |
| 2019/0112737 A1 | 4/2019 | Ashraf et al. |
| 2019/0254881 A1 | 8/2019 | Ishikawa et al. |
| 2019/0298586 A1 | 10/2019 | Ashraf et al. |
| 2019/0298587 A1 | 10/2019 | Ashraf et al. |
| 2019/0246196 A1 | 12/2019 | Han et al. |
| 2019/0374392 A1 | 12/2019 | Ninomiya et al. |
| 2019/0374404 A1 | 12/2019 | Ninomiya et al. |
| 2020/0155370 A1 | 5/2020 | Ohtsubo |
| 2020/0155371 A1 | 5/2020 | Ohtsubo |
| 2020/0206040 A1 | 7/2020 | Andrews et al. |

(56) References Cited

U.S. PATENT DOCUMENTS

| | | | |
|---|---|---|---|
| 2020/0214901 A1 | 7/2020 | Andrews et al. | |
| 2020/0298545 A1 | 9/2020 | Andrews et al. | |

FOREIGN PATENT DOCUMENTS

| | | |
|---|---|---|
| CN | 1685099 | 10/2005 |
| CN | 101746057 A | 6/2010 |
| CN | 105997351 A | 10/2016 |
| EP | 0989218 A1 | 3/2000 |
| EP | 1305248 B1 | 5/2003 |
| EP | 1452157 A1 | 9/2004 |
| EP | 1473148 A1 | 11/2004 |
| EP | 1393701 B1 | 7/2013 |
| EP | 3056176 A1 | 8/2016 |
| EP | 3 092 997 B1 | 8/2017 |
| EP | 3092997 A1 | 8/2017 |
| EP | 3251642 A1 | 12/2017 |
| EP | 3257488 A1 | 12/2017 |
| EP | 3563817 A1 | 11/2019 |
| JP | 3213543 A | 9/1991 |
| JP | H03213543 | 9/1991 |
| JP | H0430847 A | 2/1992 |
| JP | H06254117 | 9/1994 |
| JP | 8071107 A | 3/1996 |
| JP | H08071107 A | 3/1996 |
| JP | H08132576 A | 5/1996 |
| JP | 2000026015 A | 1/2000 |
| JP | 2000160460 | 6/2000 |
| JP | 3086141 B2 | 9/2000 |
| JP | 2002035029 A | 2/2002 |
| JP | 2002178428 A | 6/2002 |
| JP | 2002248127 A | 9/2002 |
| JP | 2003521949 | 7/2003 |
| JP | 2004081365 | 3/2004 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005320636 A | 11/2005 |
| JP | 2006149747 A | 6/2006 |
| JP | 2006149749 A | 6/2006 |
| JP | 2006204673 A | 12/2006 |
| JP | 2007190397 A | 8/2007 |
| JP | 2008029749 A | 2/2008 |
| JP | 2008055198 A | 3/2008 |
| JP | 2008104853 | 5/2008 |
| JP | 2008105425 A | 5/2008 |
| JP | 2008154998 | 5/2008 |
| JP | 2008148942 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 | 10/2008 |
| JP | 2008260131 A | 10/2008 |
| JP | 2014188042 | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009039341 A | 2/2009 |
| JP | 2009056156 A | 3/2009 |
| JP | 2009106667 | 5/2009 |
| JP | 2009172231 A | 8/2009 |
| JP | 2009240804 A | 10/2009 |
| JP | 2009241607 A | 10/2009 |
| JP | 2010131833 A | 6/2010 |
| JP | 2011015707 | 1/2011 |
| JP | 2011111165 | 6/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012115358 A | 6/2012 |
| JP | 2012521498 | 9/2012 |
| JP | 5124187 B2 | 11/2012 |
| JP | 5124188 B2 | 11/2012 |
| JP | 2013138795 A | 7/2013 |
| JP | 2014111222 | 6/2014 |
| JP | 2014097257 | 10/2014 |
| JP | 2015510831 | 4/2015 |
| JP | 2015521499 | 7/2015 |
| JP | 2016013687 A | 1/2016 |
| JP | 2016016536 A | 2/2016 |
| JP | 5942819 B2 | 6/2016 |
| JP | 2016193199 A | 11/2016 |
| JP | 6149635 B2 | 6/2017 |
| JP | 2020054741 A | 4/2018 |
| JP | 2020054742 A | 4/2018 |
| JP | 2020054744 A | 4/2018 |
| JP | 2020054745 A | 4/2018 |
| JP | 2019081304 | 5/2019 |
| JP | 2019166804 | 10/2019 |
| JP | 2019181807 | 10/2019 |
| WO | WO2017105997 | 3/1996 |
| WO | WO2008123348 | 2/2013 |
| WO | WO2003015681 | 6/2013 |
| WO | WO20140084168 A1 | 6/2014 |
| WO | WO2013084977 | 11/2014 |
| WO | WO 2016047320 A1 | 3/2016 |
| WO | WO2016056092 A1 | 4/2016 |
| WO | WO2016056093 A1 | 4/2016 |
| WO | WO2016063346 A1 | 4/2016 |
| WO | WO2016067387 A1 | 5/2016 |
| WO | WO2016071981 A1 | 5/2016 |
| WO | WO2016075974 A1 | 5/2016 |
| WO | WO2016098416 A1 | 6/2016 |
| WO | WO2016104412 A1 | 6/2016 |
| WO | WO2016104422 A1 | 6/2016 |
| WO | WO2016158499 A1 | 10/2016 |
| WO | WO2016158746 A1 | 10/2016 |
| WO | WO2016208502 A1 | 12/2016 |
| WO | WO2016208513 A1 | 12/2016 |
| WO | WO2014196669 | 6/2017 |
| WO | WO 2018061288 | 4/2018 |
| WO | WO 2018084145 | 5/2018 |
| WO | WO 2018154680 A1 | 8/2018 |
| WO | WO 2018154682 A1 | 8/2018 |
| WO | WO 2018167836 A1 | 8/2018 |
| WO | WO 2019046363 | 3/2019 |
| WO | WO 2019111203 | 6/2019 |
| WO | WO 2019150802 A1 | 8/2019 |
| WO | WO 2020006996 | 1/2020 |

OTHER PUBLICATIONS

All Office Actions, U.S. Appl. No. 15/831,464.
All Office Actions, U.S. Appl. No. 15/832,929.
All Office Actions, U.S. Appl. No. 15/833,057.
All Office Actions, U.S. Appl. No. 15/838,405.
All Office Actions, U.S. Appl. No. 15/839,896.
All Office Actions, U.S. Appl. No. 15/846,382.
All Office Actions, U.S. Appl. No. 16/115,617.
3D Nonwovens Developments for textured nonwovens; Detlef Frey; http://web.archive.org/web/20170919080326/https://www.reicofil.com/en/pages/3d_nonwovens, Sep. 19, 2017.
American Cancer Society—What Cancer Patients Their Families and Caregivers Need to Know About COVID 19—Is Impacting Our Patient Services.
ASTM—Standard Tables of Body Measurements for Adult Females Misses Figure Type Size Range 00-20.
ASTM—Standard Tables of Body Measurements for Children Infant Size—Preemie to 24 Months.

* cited by examiner

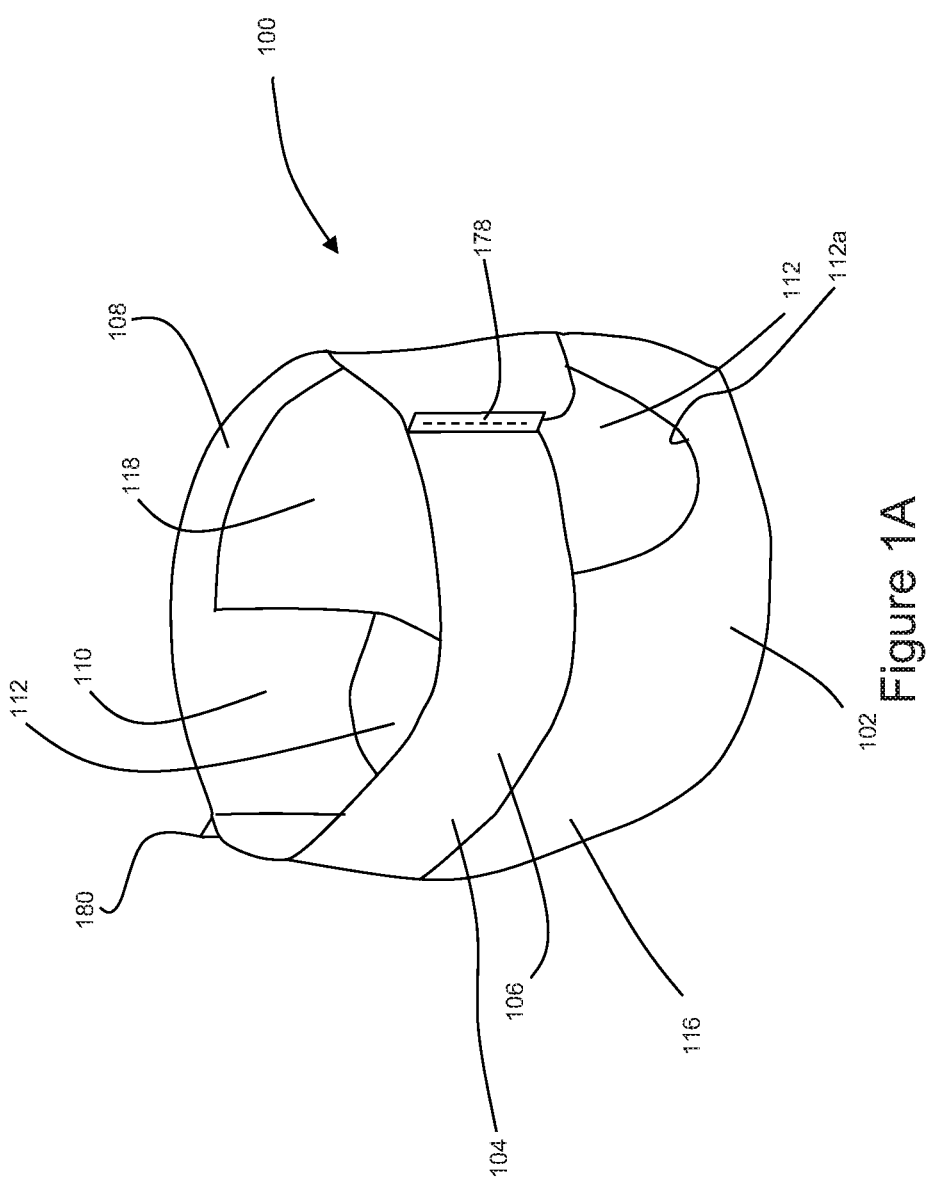

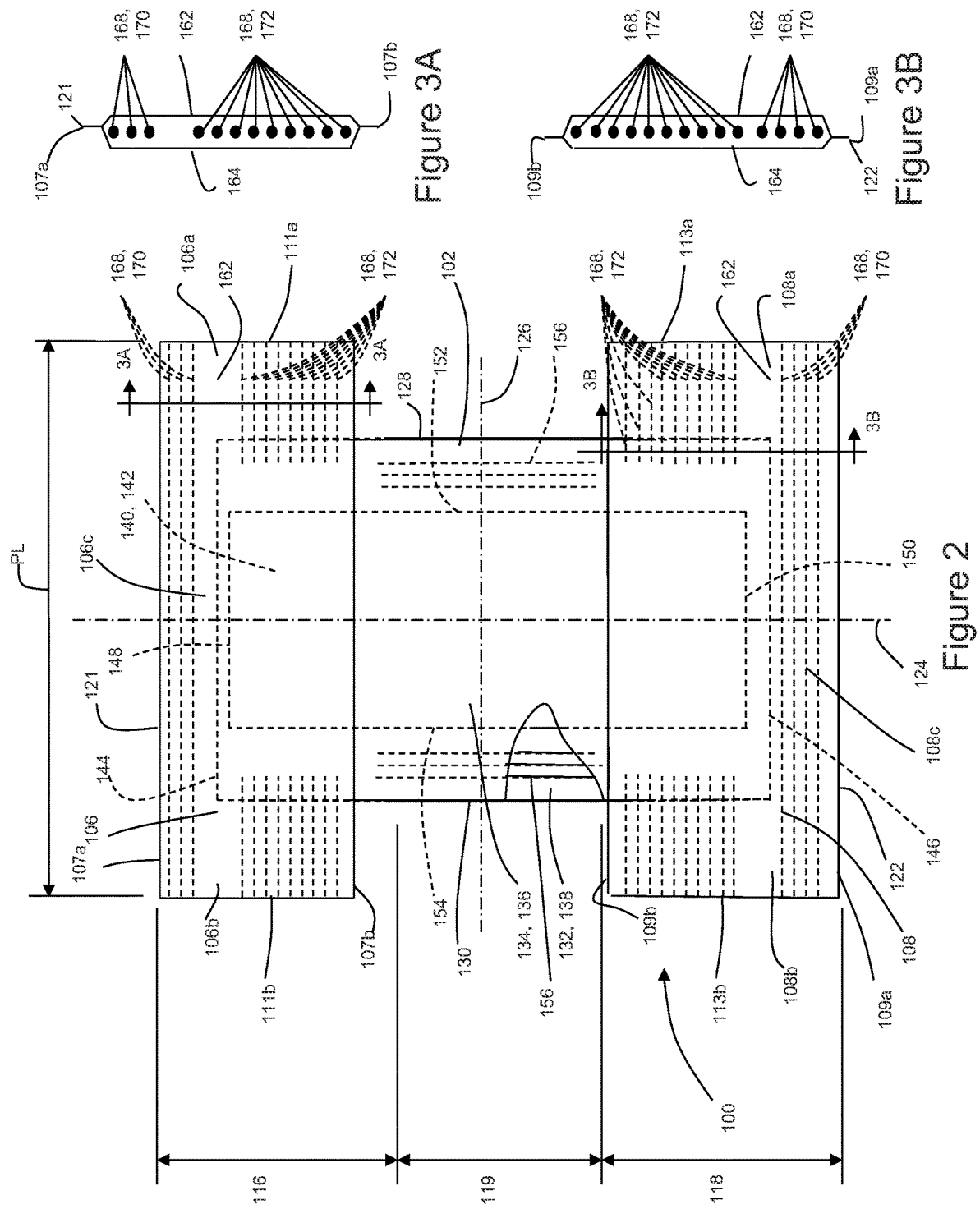

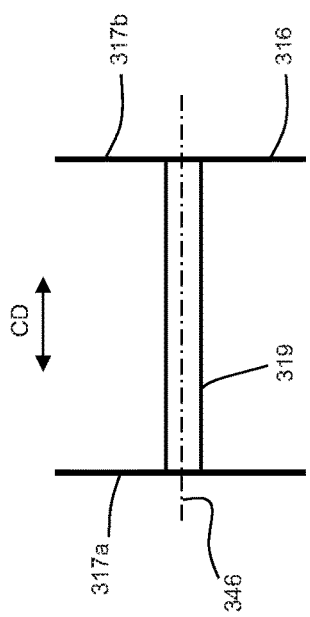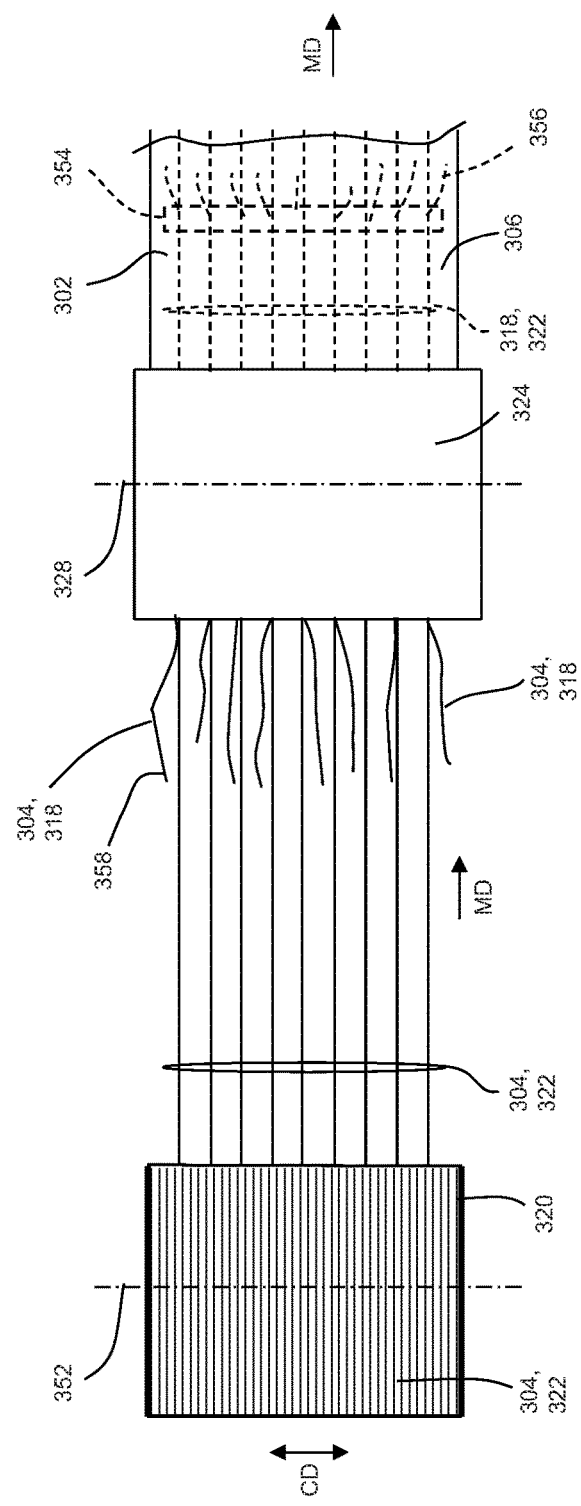

METHODS AND APPARATUSES FOR MAKING ELASTOMERIC LAMINATES WITH ELASTIC STRANDS UNWOUND FROM BEAMS

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands, and in turn, forms corrugations. The resulting elastomeric laminate is stretchable to the extent that the corrugations allow the elastic strands to elongate.

In some assembly processes, stretched elastic strands may be advanced in a machine direction and adhered between two advancing substrates, wherein the stretched elastic strands are spaced apart from each other in a cross direction. Some assembly processes are also configured with several elastic strands that are very closely spaced apart from each other in the cross direction. In some configurations, close cross directional spacing between elastic strands can be achieved by drawing elastic strands from windings that have been stacked in the cross direction on a beam. For example, various textile manufacturers may utilize beam elastics and associated handling equipment, such as available from Karl Mayer Corporation. However, problems can be encountered in manufacturing processes when drawing elastic strands stacked on a beam. For example, when elastic strands are completely drawn from the beam, a new beam of elastics will be needed to replace the empty beam. As such, in some configurations, an entire manufacturing line may need to be temporarily stopped while the empty beam is replaced.

Manufacturing lines in the textile industry often operate at relatively slow speeds, and as such, these textile manufacturing lines can be temporarily stopped to replace an empty beam and may not result in a major disruption to production. However, some manufacturing lines, such as disposable absorbent article manufacturing lines, may operate at high speeds and/or would require depleted beams of elastics to be replaced relatively often. As such, it can be inefficient and/or cost prohibitive to frequently stop and restart high speed manufacturing operations to replace empty beams.

Consequently, it would be beneficial to provide a method and apparatus for producing elastomeric laminates with beams of elastic strands that can be replaced without having to stop the assembly process.

SUMMARY OF THE INVENTION

In a first aspect, a method for making an elastomeric laminate comprises the steps of: providing a first plurality of elastic strands wound onto a first beam; providing a second plurality of elastic strands wound onto a second beam; rotating a first roller about a first axis of rotation extending in a cross direction, the first roller comprising an outer circumferential surface comprising a surface speed $V1$; rotating a second roller about a second axis of rotation extending in the cross direction, the second roller comprising an outer circumferential surface comprising a surface speed $V1$, wherein the first roller and the second roller rotate in opposite directions, and wherein the first roller is adjacent the second roller to define a nip between the first roller and the second roller; advancing a first substrate and a second substrate through the nip; rotating the first beam to unwind the first plurality of elastic strands from the first beam in a machine direction at a speed $V2$, wherein the first plurality of elastic strands are separated from each other in the cross direction, and wherein $V2$ is less than $V1$; stretching the first plurality of elastic strands in the machine direction by advancing the first plurality of elastic strands from the first beam through the nip and between the first substrate and the second substrate; connecting the second plurality of elastic strands with a splicer member; rotating the second beam to unwind the second plurality of elastic strands from the second beam in the machine direction, wherein the second plurality of elastic strands are separated from each other in the cross direction; advancing the splicer member and the second plurality of elastic strands through the nip; and discontinuing advancement of the first plurality of elastic strands through the nip subsequent to advancing the splicer member through the nip.

In another aspect, a method for making an elastomeric laminate comprises the steps of: providing a first plurality of elastic strands wound onto a first beam; providing a second plurality of elastic strands wound onto a second beam; rotating a first roller about a first axis of rotation extending in a cross direction, the first roller comprising an outer circumferential surface comprising a surface speed $V1$; providing a first substrate comprising a first surface and an opposing second surface; advancing the first surface of the first substrate onto the outer circumferential surface of the first roller; rotating the first beam to unwind the first plurality of elastic strands from the first beam in a machine direction at a speed $V2$, wherein the first plurality of elastic strands are separated from each other in the cross direction, and wherein $V2$ is less than $V1$; stretching the first plurality of elastic strands in the machine direction by advancing the first plurality of elastic strands from the first beam onto second surface of the first substrate; advancing the combined first substrate and the first plurality of elastic strands in the machine direction from the first roller; connecting the second plurality of elastic strands with a splicer member; rotating the second beam to unwind the second plurality of elastic strands from the second beam in the machine direction, wherein the second plurality of elastic strands are separated from each other in the cross direction; combining the splicer member and the second plurality of elastic strands with the first plurality of elastic strands on the second surface of the first substrate; and subsequently discontinuing advancement of the first plurality of elastic strands onto the second surface of the first substrate.

In yet another aspect, a method for making an elastomeric laminate comprises the steps of: providing a first plurality of elastic strands wound onto a first beam; providing a second plurality of elastic strands wound onto a second beam; rotating a roller about a first axis of rotation extending in a cross direction, the roller comprising an outer circumferential surface; providing a first substrate and a second substrate, each comprising a first surface and an opposing second surface; advancing the first surface of the first substrate onto the outer circumferential surface of the roller; rotating the first beam to unwind the first plurality of elastic strands from the first beam in a machine direction, wherein the first plurality of elastic strands are separated from each other in the cross direction; stretching the first plurality of elastic strands in the machine direction while advancing the first plurality of elastic strands from the first beam onto the second surface of the first substrate; advancing the first surface of the second substrate onto the second surface of the first substrate such that the first plurality of elastic strands and the first substrate are positioned between the second substrate and the outer circumferential surface of the roller; advancing the combined first substrate, second substrate, and the first plurality of elastic strands in the machine direction from the roller; rotating the second beam to unwind the second plurality of elastic strands from the second beam in the machine direction, wherein the second plurality of elastic strands are separated from each other in the cross direction; advancing the second plurality of elastic strands in between the second surface of the first substrate and the first surface of the second substrate such that the first plurality of elastic strands, the second plurality of elastic strands, and the first substrate are positioned between the second substrate and the outer circumferential surface of the roller; and subsequently discontinuing advancement of the first plurality of elastic strands onto the second surface of the first substrate.

BRIEF DESCRIPTION OF THE DRAWINGS

FIG. 1A is a front perspective view of a diaper pant.
FIG. 2 is a partially cut away plan view of the diaper pant shown in FIGS. 1A and 1B in a flat, uncontracted state.
FIG. 3A is a cross-sectional view of the diaper pant of FIG. 2 taken along line 3A-3A.
FIG. 3B is a cross-sectional view of the diaper pant of FIG. 2 taken along line 3B-3B.

FIG. 9 is a view of the converting apparatus of FIG. 8 taken along line 9-9.
FIG. 10 is a view of the converting apparatus of FIG. 8 taken along line 10-10.

DETAILED DESCRIPTION OF THE INVENTION

Figure 1B:
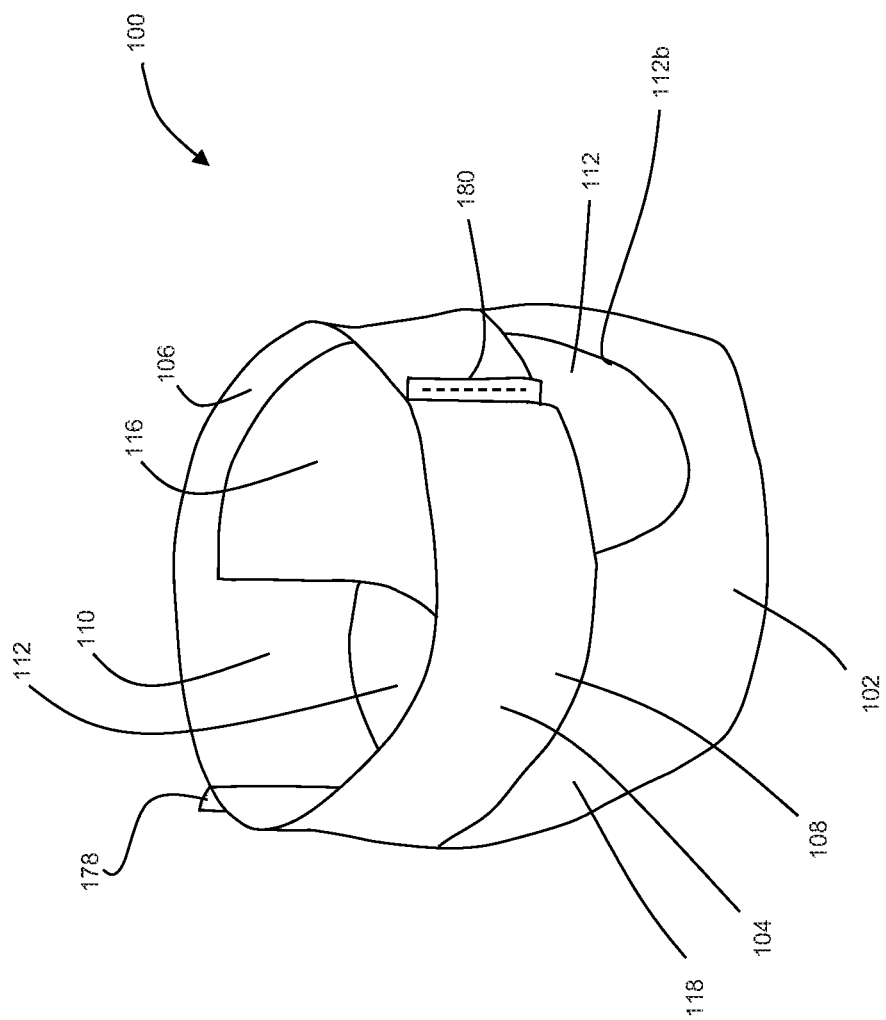
FIG. 1B is a rear perspective view of a diaper pant.

The following term explanations may be useful in understanding the present disclosure:
"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations in U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The present disclosure relates to methods for manufacturing absorbent articles, and in particular, to methods for making elastomeric laminates that may be used as components of absorbent articles. The elastomeric laminates may include a first substrate, a second substrate, and an elastic material located between the first substrate and second substrate. During the process of making the elastomeric laminate, the elastic material may be advanced and stretched in a machine direction and may be joined with either or both the first and second substrates advancing in the machine direction.

The methods and apparatuses according to the present disclosure may be configured with a first plurality of elastic strands wound onto a first beam and a second plurality of elastic strands wound onto a second beam. During assembly of an elastomeric laminate, a first substrate is advanced onto the outer circumferential surface of the roller that is rotating about a first axis of rotation extending in a cross direction. The first beam is rotated to unwind the first plurality of elastic strands from the first beam in the machine direction. The first plurality of elastic strands may be stretched in the machine direction while advancing from the first beam onto the first substrate. A second substrate advances onto the first substrate such that the first plurality of elastic strands are positioned between the first substrate and the second substrate to form the elastomeric laminate. Before the first plurality of elastic strands are completely unwound from the first beam, the second beam is rotated to unwind the second plurality of elastic strands from the second beam in the machine direction, wherein the second plurality of elastic strands are separated from each other in the cross direction. The second plurality of elastic strands are advanced in the machine direction from the second beam to between the first substrate and the second substrate such that the first and plurality of elastic strands are positioned between the first and second substrates. Subsequently, the advancement of the first plurality of elastic strands from the first beam is discontinued. As such, the elastomeric laminate assembly process may continue uninterrupted while switching from an initially utilized elastic material drawn from the first beam to a subsequently utilized elastic material drawn from the second beam.

As previously mentioned, the elastomeric laminates made according to the processes and apparatuses discussed herein may be used to construct various types of components used in the manufacture of different types of absorbent articles, such as diaper pants and taped diapers. To help provide additional context to the subsequent discussion of the process embodiments, the following provides a general description of absorbent articles in the form of diapers that include components including the elastomeric laminates that may be produced with the methods and apparatuses disclosed herein.

FIGS. 1A, 1B, and 2 show an example of a diaper pant 100 that may include components constructed from elastomeric laminates assembled in accordance with the apparatuses and methods disclosed herein. In particular, FIGS. 1A and 1B show perspective views of a diaper pant 100 in a pre-fastened configuration, and FIG. 2 shows a plan view of the diaper pant 100 with the portion of the diaper that faces away from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100 may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100 may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, apparatuses and methods according to the present disclosure may be utilized to produce elastomeric laminates that may be used to construct various components of diapers, such as elastic belts, leg cuffs, and the like. For example, FIGS. 4-23 show schematic views of converting apparatuses 300 adapted to manufacture elastomeric laminates 302. As described in more detail below, the converting apparatuses 300 shown in FIGS. 4-23 operate to advance a continuous length of elastic material 304, a continuous length of a first substrate 306, and a continuous length of a second substrate 308 along a machine direction MD. It is also to be appreciated that in some configurations, the first substrate and second substrate 306, 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

The elastomeric laminates 302 can be used to construct various types of diaper components. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may be used to construct waistbands and/or side panels in taped diaper configurations. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, a metering device may comprise a beam of elastic strands wound thereon. During operation, elastic material may advance in a machine direction from a first rotating beam to a downstream metering device to be joined with one or more advancing substrates. Before the elastic material is completely drawn from or removed from the first beam, elastic material may also be advanced in the machine direction from a second rotating beam to the downstream metering device to be joined with one or more advancing substrates. Subsequently, advancement of the elastic material from the first beam to the downstream metering device may be discontinued. As such, the elastomeric laminate assembly process continues uninterrupted while replacing elastic material unwound from the first beam with elastic material unwound from the second beam. Thus, the empty first beam may be replaced with another beam with elastic material wound thereon without interrupting and/or stopping the assembly of the elastomeric laminate.

Figure 4:
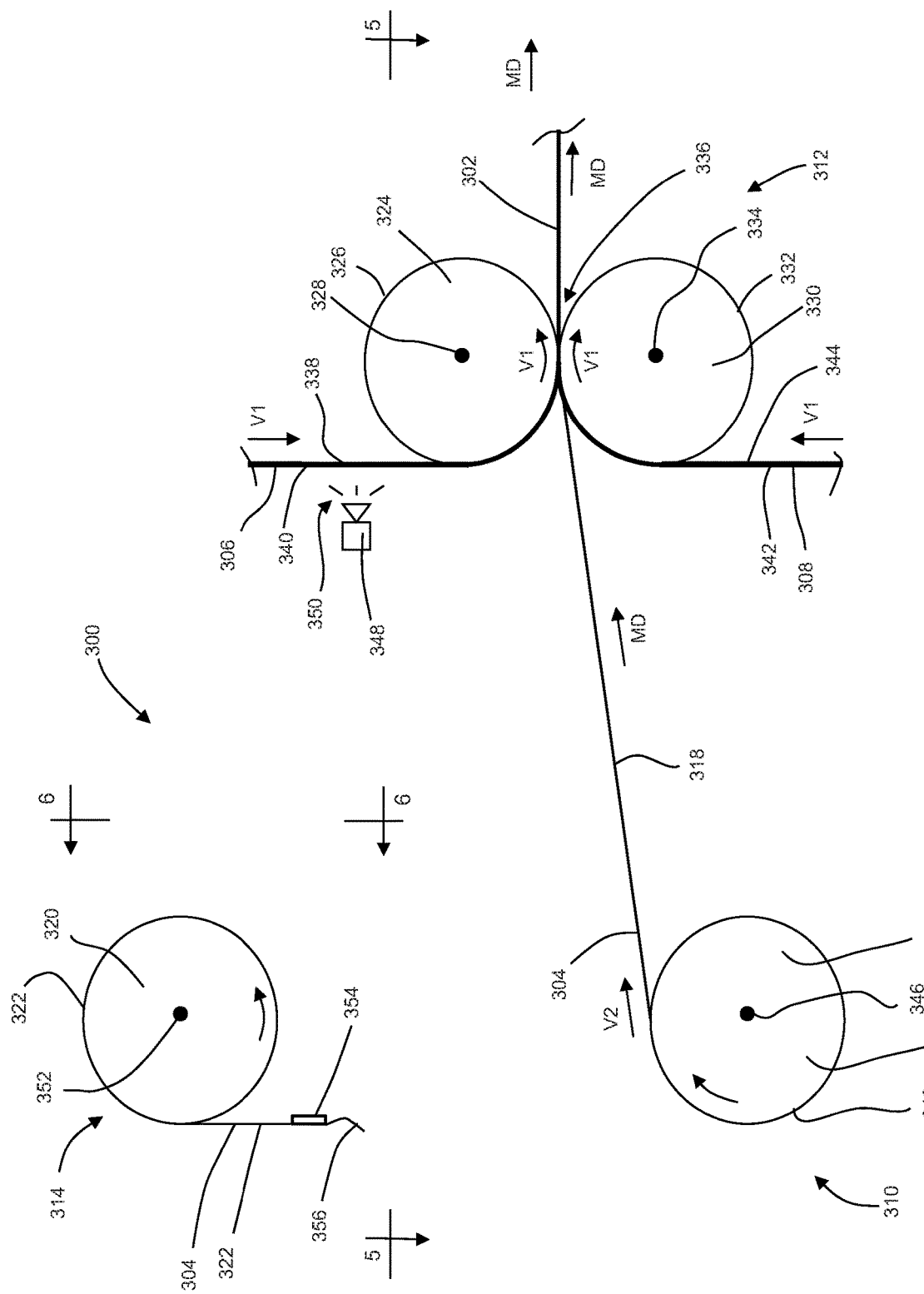
FIG. 4 is a schematic side view of a converting apparatus adapted to manufacture an elastomeric laminate including a first plurality of elastic strands positioned between a first substrate and a second substrate.
Figure 6:
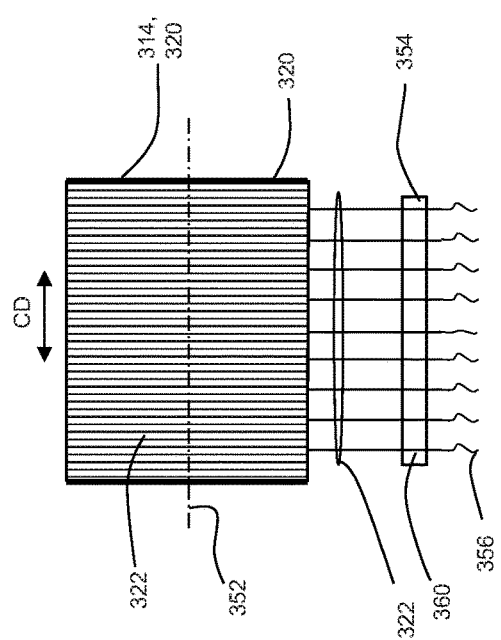
FIG. 6 is a view of the converting apparatus of FIG. 4 taken along line 6-6.
Figure 5:
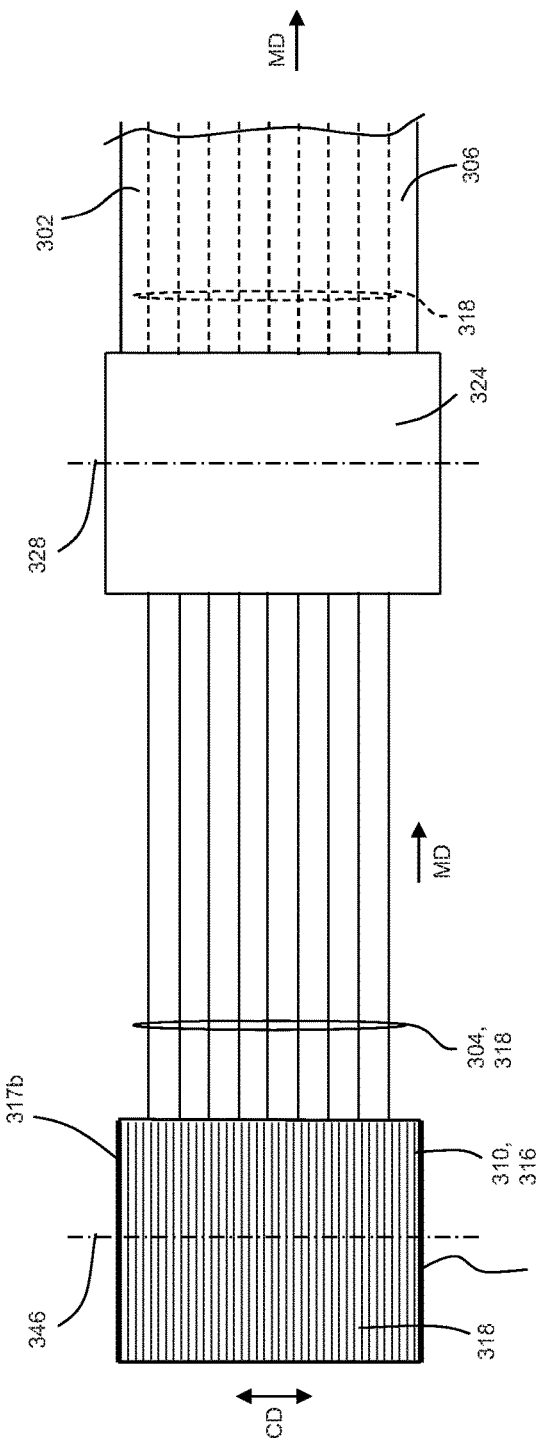
FIG. 5 is a view of the converting apparatus of FIG. 4 taken along line 5-5.

As shown in FIGS. 4-6, a converting apparatus 300 for producing an elastomeric laminate 302 may include a first metering device 310, a second metering device 312, and a third metering device 314. The first metering device may be configured as a first beam 316 with a first plurality of elastic strands 318 wound thereon, and the third metering device is configured as a second beam 320 with a second plurality of elastic strands 322 wound thereon. FIG. 10 shows an example of an empty beam 316 that includes two side plates 317a, 317b that may be connected with opposing end portions of a mandrel core 319, wherein elastic strands may be wound onto the mandrel core 319. It is to be appreciated that beams of various sizes and technical specifications may be utilized in accordance with the methods and apparatuses herein, such as for example, beams that are available from ALUCOLOR Textilmaschinen, GmbH. During operation, the first plurality of elastic strands 318 advance in the machine direction MD from the first beam 316 to the second metering device 312. In addition, the first plurality of elastic strands 318 may be stretched along the machine direction MD between the first beam 316 and the second metering device 312. The stretched first elastic strands 318 are also joined with a first substrate 306 and a second substrate 308 at the second metering device 312 to produce an elastomeric laminate 302. As discussed in more detail below, once the first beam 316 is empty or nearly depleted of first elastic strands 318, the second plurality of elastic strands 322 can be introduced into the assembly operation as replacements for the first plurality of elastic stands 318 without having to stop the assembly operation.

As shown in FIG. 4, the second metering device 312 includes: a first roller 324 having an outer circumferential surface 326 and rotates about a first axis of rotation 328, and a second roller 330 having an outer circumferential surface 332 and rotates about a second axis of rotation 334. The first roller 324 and the second roller 330 rotate in opposite directions, and the first roller 324 is adjacent the second roller 330 to define a nip 336 between the first roller 324 and the second roller 330. The first roller 324 rotates such that the outer circumferential surface 326 has a surface speed V1, and the second roller 330 may rotate such that the outer circumferential surface 332 has the same, or substantially the same, surface speed V1.

As shown in FIGS. 4 and 5, the first substrate 306 includes a first surface 338 and an opposing second surface 340, and the first substrate 306 advances to the first roller 324. In particular, the first substrate 306 advances at speed V1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 330. In particular, the second substrate 308 advances at speed V1 to the second roller 330 where the second substrate 308 partially wraps around the outer circumferential surface 332 of the second roller 330 and advances through the nip 336. As such, the second surface 344 of the second substrate 308 travels in the same direction as and in contact with the outer circumferential surface 332 of the second roller 330.

With continued reference to FIGS. 4 and 5, the first beam 316 includes the first plurality of elastic strands 318 wound thereon, and the first beam 316 is rotatable about a first beam rotation axis 346. In some configurations, the first beam rotation axis 346 may extend in the cross direction CD. As the first beam 316 rotates, the first plurality of elastic strands 318 advance from the first beam 316 at a speed V2 with the first elastic strands 318 being spaced apart from each other in the cross direction CD. From the first beam 316, the first plurality of elastic strands 318 advances in the machine direction MD to the nip 336. In some configurations, the speed V2 is less than the speed V1, and as such, the first plurality of elastic strands 318 are stretched in the machine direction MD. In turn, the stretched first elastic strands 318 advance through the nip 336 between the first and second substrates 306, 308 such that the first elastic strands 318 are joined with the second surface 340 of the first substrate 306 and the first surface 342 of the second substrate 308 to produce a continuous length of elastomeric laminate 302. As shown in FIG. 4, the first substrate 306 may advance past an adhesive applicator device 348 that applies adhesive 350 to the second surface 340 of the first substrate 306 before advancing to the nip 336. It is to be appreciated that the adhesive 350 may be applied to the first substrate 306 upstream of the first roller 324 and/or while the first substrate 306 is partially wrapped around the outer circumferential surface 326 of the first roller 324. It is to be appreciated that adhesive may be applied to the first elastic strands 318 before and/or while being joined with first substrate 306 and second substrate 308. In addition, it is to be appreciated that adhesive may be applied to the first surface 342 of the second substrate 308 before or while being joined with the first elastic strands 318 and the first substrate 306.

Figure 7:
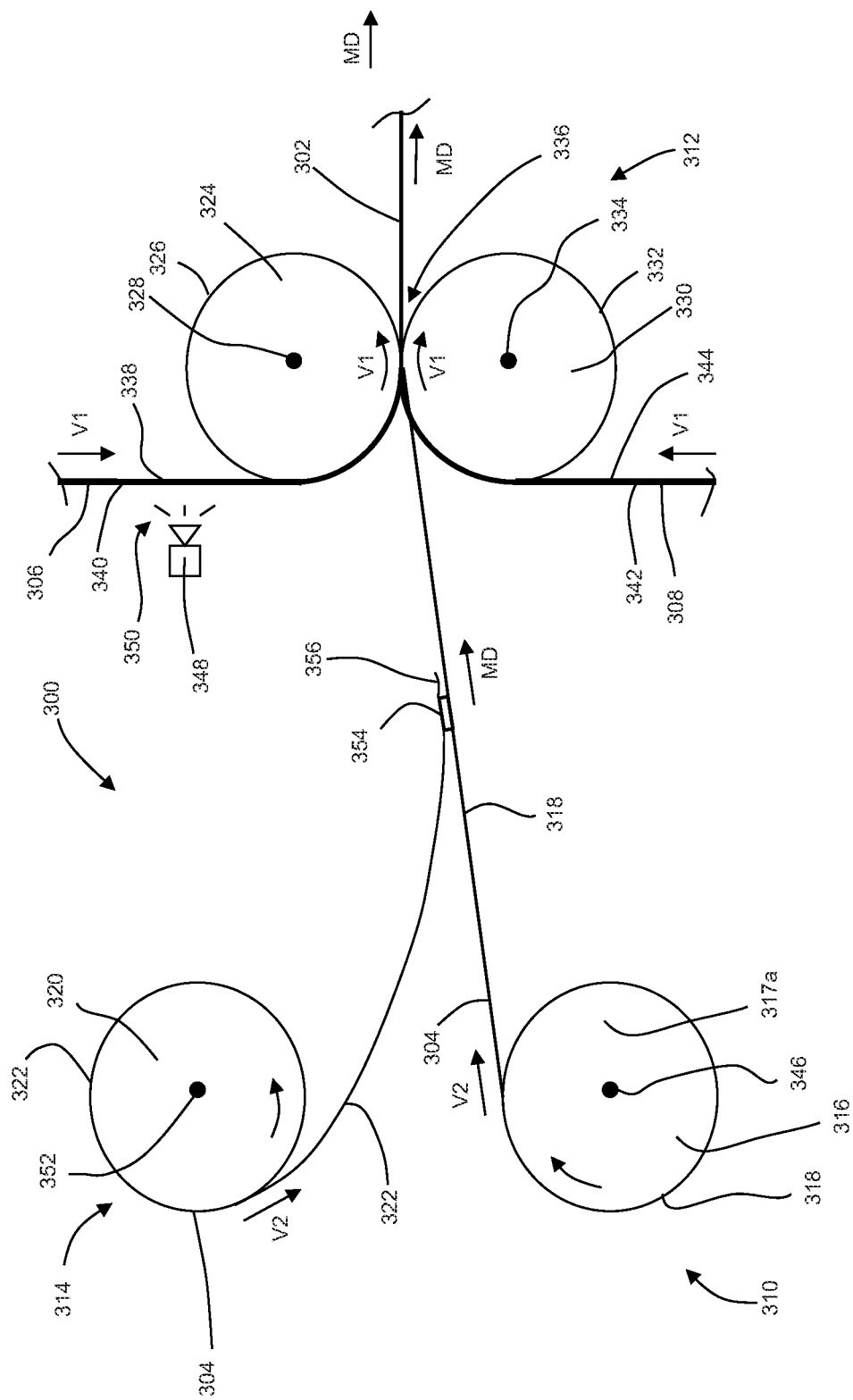
FIG. 7 is a schematic side view of the converting apparatus of FIG. 4 showing a second plurality of elastic strands connected with a first plurality of elastic strands upstream of a nip.
Figure 8:
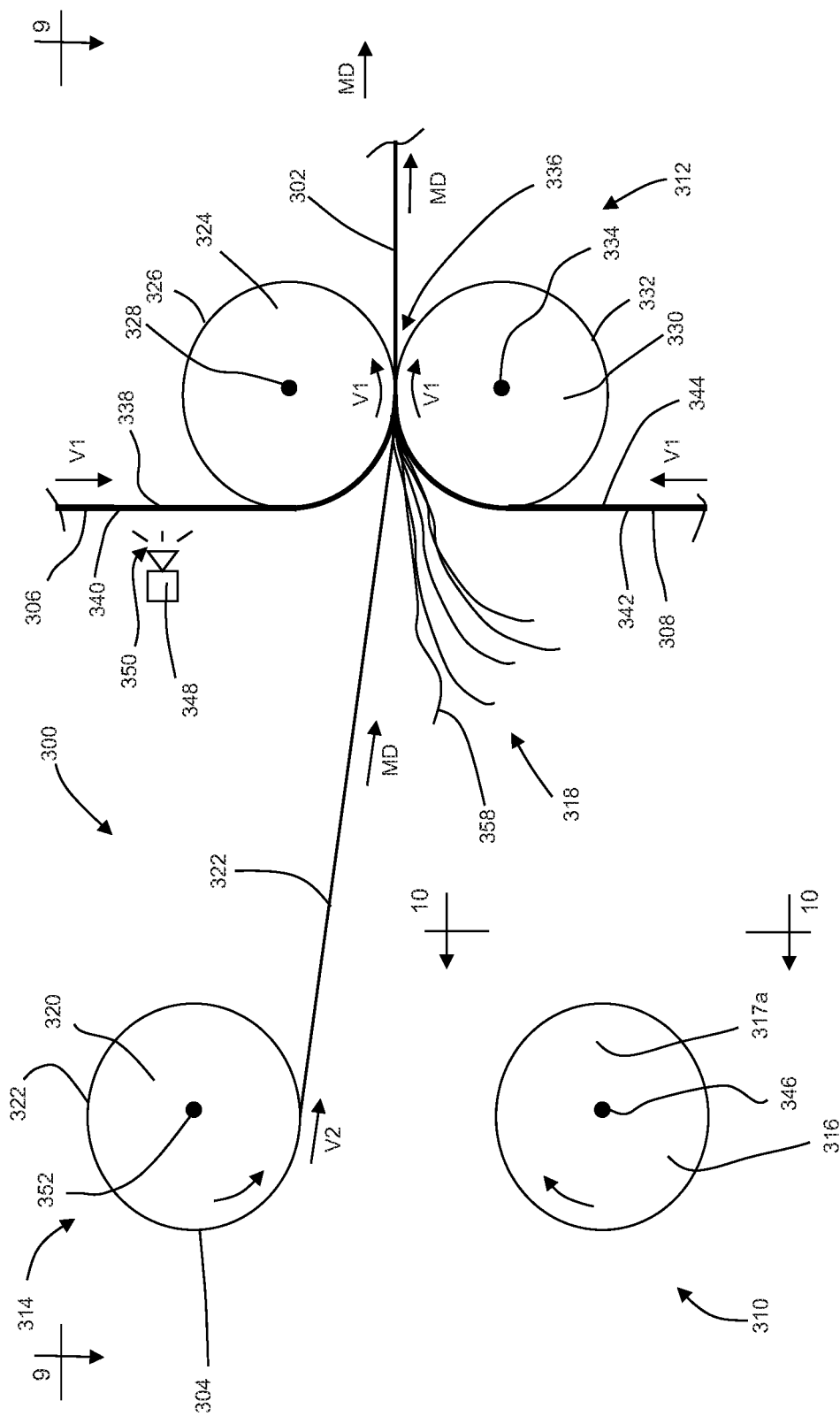
FIG. 8 is a schematic side view of the converting apparatus of FIG. 4 showing the first and second plurality of elastic strands advancing through the nip.

As previously discussed, the apparatus 300 includes the second plurality of elastic strands 322 configured to replace the first plurality of elastic stands 318 once the first beam 316 is completely depleted or nearly depleted of first elastic strands 318. As shown in FIGS. 4 and 6, the second beam 320 includes the second plurality of elastic strands 322 wound thereon, and the second beam 320 is rotatable about a second beam rotation axis 352. In some configurations, the second beam rotation axis 352 may extend in the cross direction CD. As the second beam 320 rotates, the second plurality of elastic strands 322 advance from the second beam 320 at a speed V2 with the second elastic strands 322 being spaced apart from each other in the cross direction CD. When introducing the second elastic strands 322 into the assembly operation, the second plurality of elastic strands 322 may first be connected with a splicer member 354. As shown in FIG. 6, the splicer member 354 may be connected adjacent leading ends 356 of the second elastic strands 322. In turn, the splicer member 354 and the second elastic strands 322 may be connected with the first plurality of elastic strands 318 that are advancing from the first beam 316 to the nip 336 as shown in FIG. 7. As shown in FIGS. 8 and 9, the splicer member 354 and the leading ends 356 of the second plurality of elastic strands 322 advance in the machine direction MD and are positioned between the first and second substrates 306, 308 along with the first plurality of elastic strands 318. Once the second elastic strands 322 are combined with the first substrate 306 and/or second substrate 308, advancement of the first plurality of elastic strands 318 from the first beam 316 may be discontinued. In some instances, advancement of the first plurality of elastic strands 318 from the first beam 316 may be discontinued as a result of the first elastic strands 318 being completely unwound from the first beam 316 such that trailing ends 358 of the first elastic strands 318 advance through the nip 336 such as shown in FIGS. 8-10. In some configurations, the first elastic strands 318 may be cut to discontinue advancement from the first beam 316.

Figure 11:
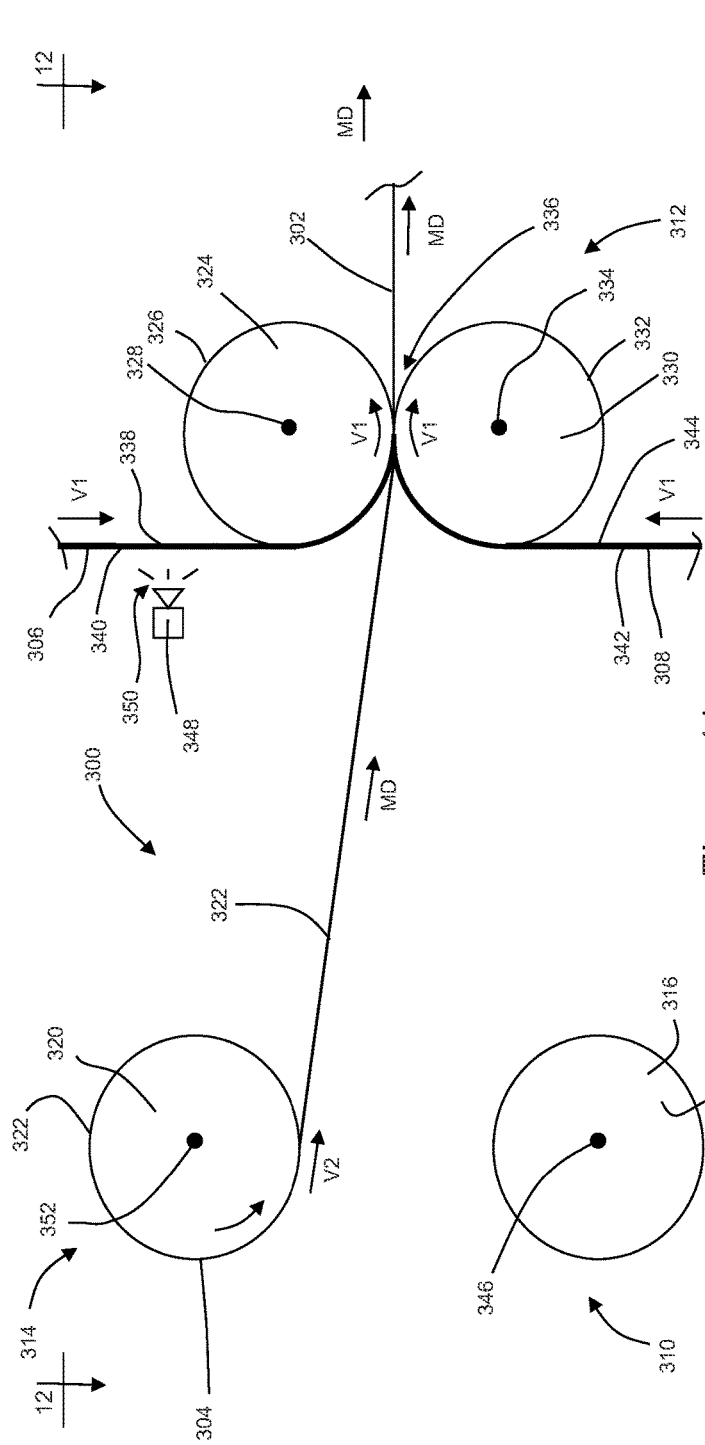
FIG. 11 is a schematic side view of the converting apparatus of FIG. 4 assembling the elastomeric laminate with the second plurality of elastic strands positioned between the first and second substrates.
Figure 12:
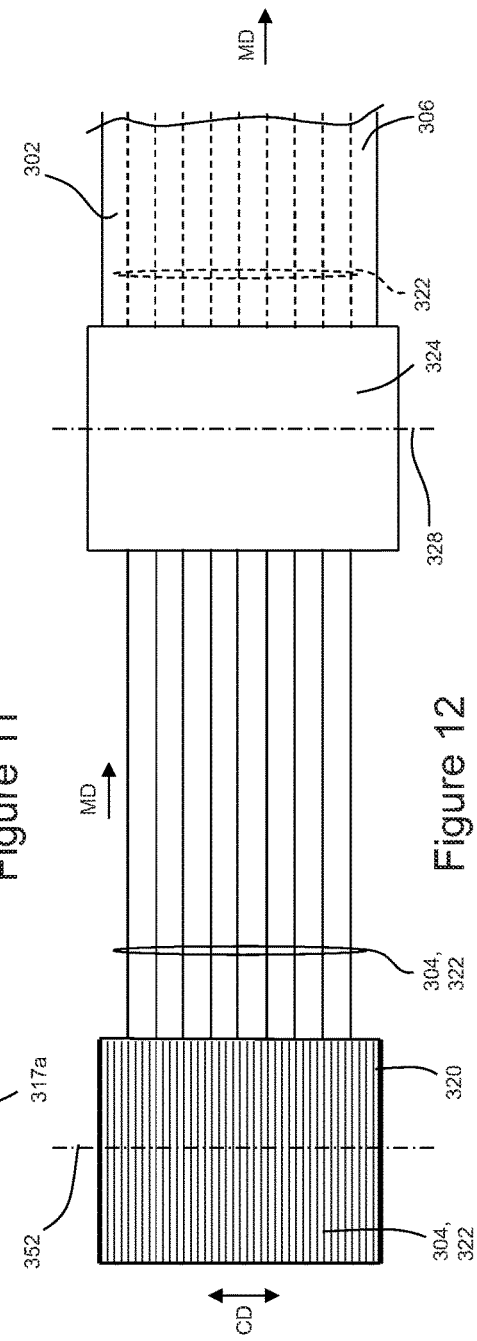
FIG. 12 is a view of the converting apparatus of FIG. 11 taken along line 12-12.

As shown in FIGS. 11 and 12, the apparatus 300 continues to operate to assemble the elastomeric laminate 302 with the second plurality of elastics 322 on the second beam 320. As the second beam 320 rotates, the second plurality of elastic strands 322 advance from the second beam 320 at a speed V2 with the second elastic strands 322 being spaced apart from each other in the cross direction CD. From the second beam 320, the second plurality of elastic strands 322 advances in the machine direction MD to the nip 336. In some configurations, the speed V2 is less than the speed V1, and as such, the second plurality of elastic strands 322 are stretched in the machine direction MD. In turn, the stretched second elastic strands 322 advance through the nip 336 between the first and second substrates 306, 308 such that the second elastic strands 322 are joined with the second surface 340 of the first substrate 306 and the first surface 342 of the second substrate 308 to produce the continuous length of elastomeric laminate 302. Thus, the second plurality of elastic strands 322 can be introduced into the assembly operation as replacements for the first plurality of elastic stands 318 without having to stop rotation of the first beam 316 and without having to stop the elastomeric laminate 302 assembly operation. In turn, the empty first beam 316, such as shown in FIG. 10, can be replaced with a beam having a plurality of elastics wound thereon positioned to replace the second plurality of elastics 322 once depleted from the second beam 320.

It is to be appreciated that the apparatus 300 can be configured to operate in various ways to advance the leading ends 356 of the second plurality of elastics 322 between the first and second substrates 306, 308. For example, the splicer member 354 discussed above with reference to FIG. 6 may include one or more tacky surfaces 360 adapted to adhere to the second plurality of elastic strands 322. In addition, the one or more tacky surfaces 360 also adhere the splicer member 354 with the advancing first plurality of elastic strands 318 as described above with reference to FIGS. 7-9. It is also to be appreciated that the splicer member 354 may be connected with the first elastic strands 318 with adhesive applied to the first elastic strands 318 upstream of the nip 336. It is also to be appreciated that in some configurations of the apparatus 300, the second elastic strands 322 may be introduced into the assembly operation without having to connect the second elastic strands 322 with a splicer member 354.

Figure 13:
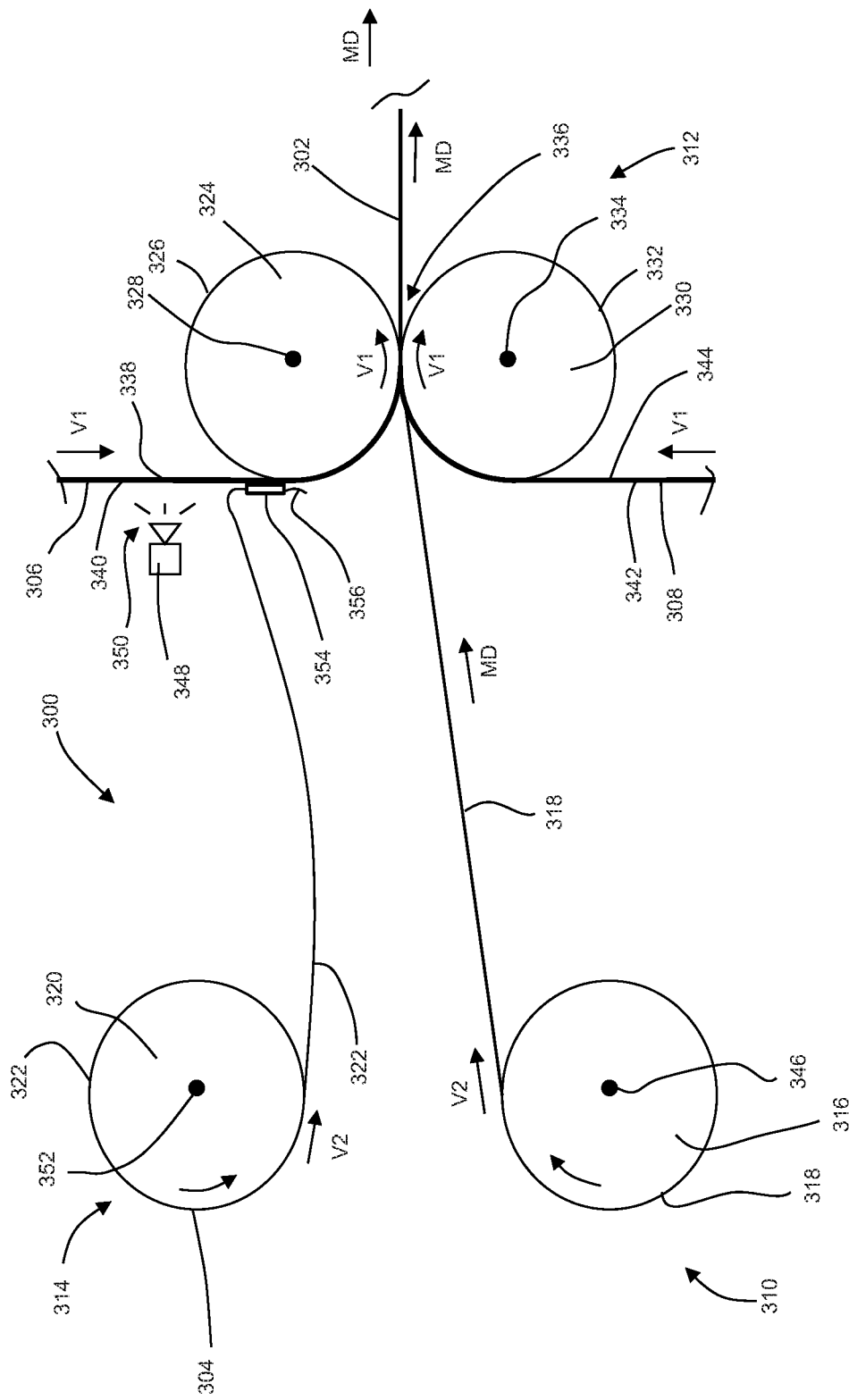
FIG. 13 is a schematic side view of the converting apparatus of FIG. 4 showing the second plurality of elastic strands connected with the first substrate upstream of a nip.

In some configurations, as opposed to being connected with the first elastic strands 318, the splicer member 354 and/or second elastic strands 322 may be connected with the first substrate 306 or the second substrate 308 upstream of the nip 336. For example, as shown in FIG. 13, after second elastic strands 322 are connected with the splicer member 354, the splicer member 354 may be connected with the second surface 340 of the first substrate 306. As discussed above, the splicer member 354 may include a tacky surface 360 that adheres to the first substrate 306 and/or may be adhered to the first substrate with adhesive 350. Once the splicer member 354 is connected with the first substrate 306, the splicer member 354 and second elastic strands 322 advance along with the first substrate 306 through the nip 336.

It is to be appreciated that different components may be used to construct the elastomeric laminates 302 in accordance with the methods and apparatuses herein. For example, the first and/or second substrates 306, 308 may include nonwovens and/or films. In addition, the first and/or second elastic strands 318, 322 may be configured in various ways and having various decitex values. In some configurations, the first and/or second plurality of elastic strands 318, 322 may be configured with decitex values ranging from about 10 decitex to about 500 decitex, specifically reciting all 1 decitex increments within the above-recited range and all ranges formed therein or thereby. It is also to be appreciated the first beam 316 and the second beam 320 may be configured in various ways and with various quantities of elastic strands. Example beams, also referred to as warp beams, that may be used with the apparatus and methods herein are disclosed in U.S. Pat. Nos. 4,525,905; 5,060,881; and 5,775,380; and U.S. Patent Publication No. 2004/0219854 A1. Although FIG. 5 shows nine elastic strands 318 advancing from the first beam 316, it is to be appreciated that the apparatuses herein may be configured such that more or less than nine elastic strands 318 advance from the first beam 316. And although FIG. 6 shows nine elastic strands 322 advancing from the second beam 320, it is to be appreciated that the apparatuses herein may be configured such that more or less than nine elastic strands 322 advance from the second beam 320. In some configurations, the first elastic strands 318 advancing from the first beam 316 and/or the second elastic strands 322 advancing from the second beam 320 may include from about 100 to about 2000 strands, specifically reciting all 1 strand increments within the above-recited range and all ranges formed therein or thereby. In some configurations, the first elastic strands 318 and/or the second elastic strands 322 may be separated from each other by about 0.5 mm to about 4 mm in the cross direction, specifically reciting all 0.1 mm increments within the above-recited range and all ranges formed therein or thereby. As discussed herein, the elastics in the plurality of elastic strands may be pre-strained prior to joining the elastic strand to the first or second substrate layers 306, 308. In some configurations, the elastic may be pre-strained from about 75% to about 300%, specifically reciting all 1% increments within the above-recited range and all ranges formed therein or thereby. It is also to be appreciated that one or more beams of elastics may be arranged along the cross direction CD of a converting process and/or arranged along a machine direction MD in various different portions of a converting process. It is also to be appreciated that the first beam 316 and the second beam 320 can be connected with one or more motors, such as servo motors, to drive and control the rotation of the beams 316, 320.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 318, 322 unwound from more than one beam and/or in combination with elastic stands supplied from an overend unwinder. The elastic strands may be joined with the first and second substrates 306, 308 such that the elastomeric laminate 302 may have different stretch characteristics in different regions along the cross direction CD. For example, when the elastomeric laminate 302 is elongated, some elastic strands may exert contraction forces in the machine direction MD that are different from contraction forces exerted by other elastic strands. Such differential stretch characteristics can be achieved by stretching some elastic strands more or less than other elastic strands before joining the elastic strands with the first and second substrates 306, 308. It is also to be appreciated that the elastic strands may have various different material constructions and/or decitex values to create elastomeric laminates 302 having different stretch characteristics in different regions. In some configurations, the elastomeric laminate may have regions where the elastic strands are spaced relatively close to one another in the cross direction CD and other regions where the elastic strands are spaced relatively farther apart from each other in the cross direction CD to create different stretch characteristics in different regions. In some configurations, the elastic strands may be supplied on the beam in a stretched state, and as such, may not require additional stretching (or may require relatively less additional stretching) before being combined with the first substrate 306 and/or the second substrate 308.

Figure 14:
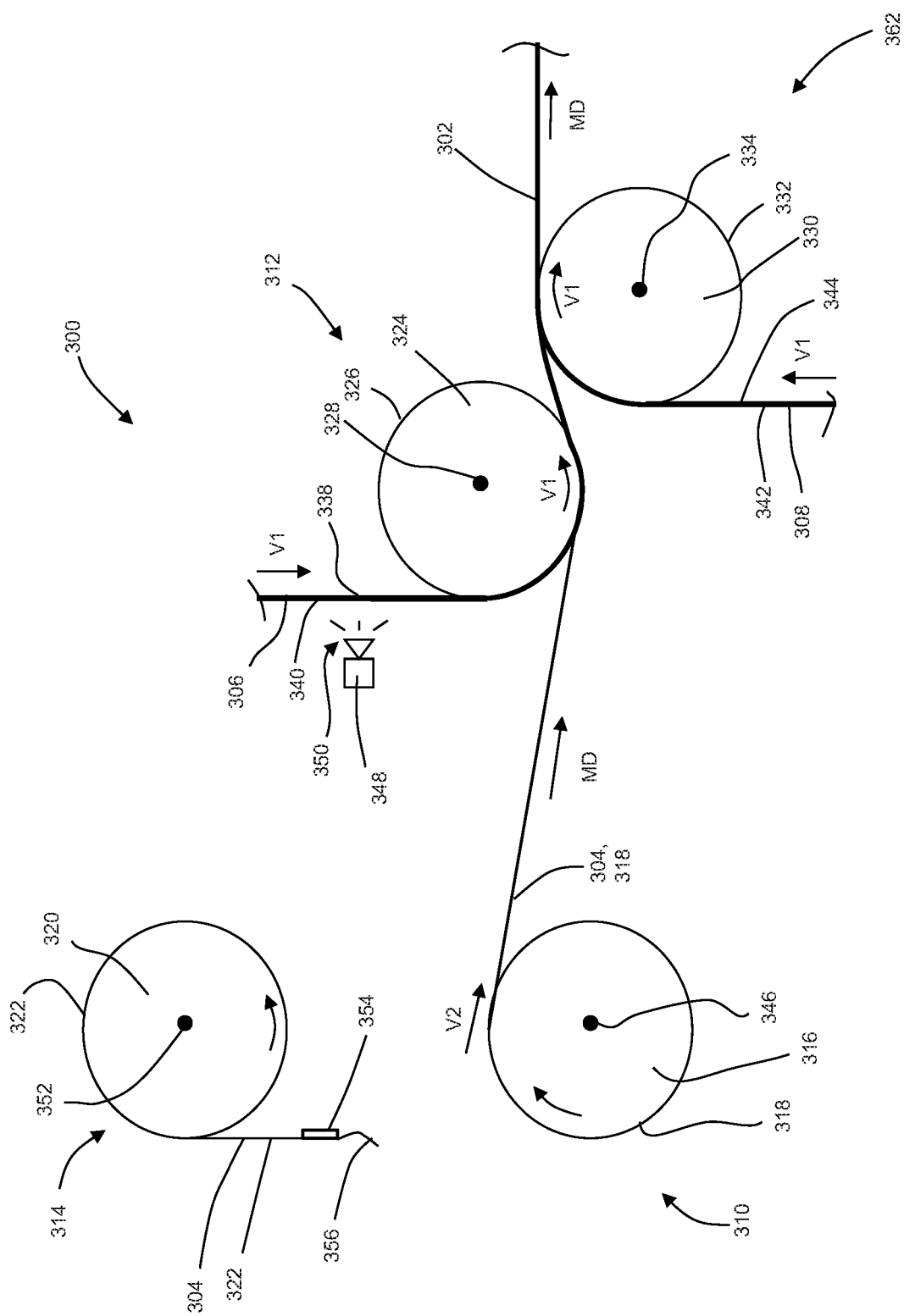
FIG. 14 is a schematic side view of a second configuration of a converting apparatus adapted to manufacture an elastomeric laminate including a first plurality of elastic strands positioned between a first substrate and a second substrate.

It is to be appreciated that the apparatuses 300 herein may be configured in various ways. For example, in a second configuration of the apparatus 300 shown in FIG. 14, the second roller 330 may be positioned downstream from the first roller 324. As such, the first roller 324 may be configured as the second metering device 312 and the second roller 330 may be configured as a fourth metering device 362. As shown in FIG. 14, the first substrate 306 advances at speed V1 to the first roller 324 where the first substrate 306 partially wraps around the outer circumferential surface 326 of the first roller 324 and advances from the first roller to the second roller 330 to be combined with second substrate 308. As the first beam 316 rotates, the first plurality of elastic strands 318 advance from the first beam 316 at a speed V2 with the first elastic strands 318 being spaced apart from each other in the cross direction CD. From the first beam 316, the first plurality of elastic strands 318 advances in the machine direction MD to the first roller 324 and are positioned on the second surface 340 of the first substrate 306. In some configurations, the speed V2 is less than the speed V1, and as such, the first plurality of elastic strands 318 are stretched in the machine direction MD.

With continued reference to FIG. 14, the first substrate 306 and the first plurality of elastic strands 318 advance from the outer circumferential surface 326 of the first roller 324 to the second roller 330. In addition, the second substrate 308 advances at speed V1 to the second roller 330 where the second substrate 308 partially wraps around the outer circumferential surface 332 of the second roller 330. In turn, the combined first substrate 306 and the stretched first elastic strands 318 advance from first roller 324 to the second roller 330 and are combined with the second substrate 308 such that the first elastic strands 318 are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the first elastic strands 318 before and/or while being joined with first substrate 306 and second substrate 308. In addition, it is to be appreciated that adhesive may be applied to the first surface 342 of the second substrate 308 before or while being joined with the first elastic strands 318 and first substrate 306.

Figure 15:
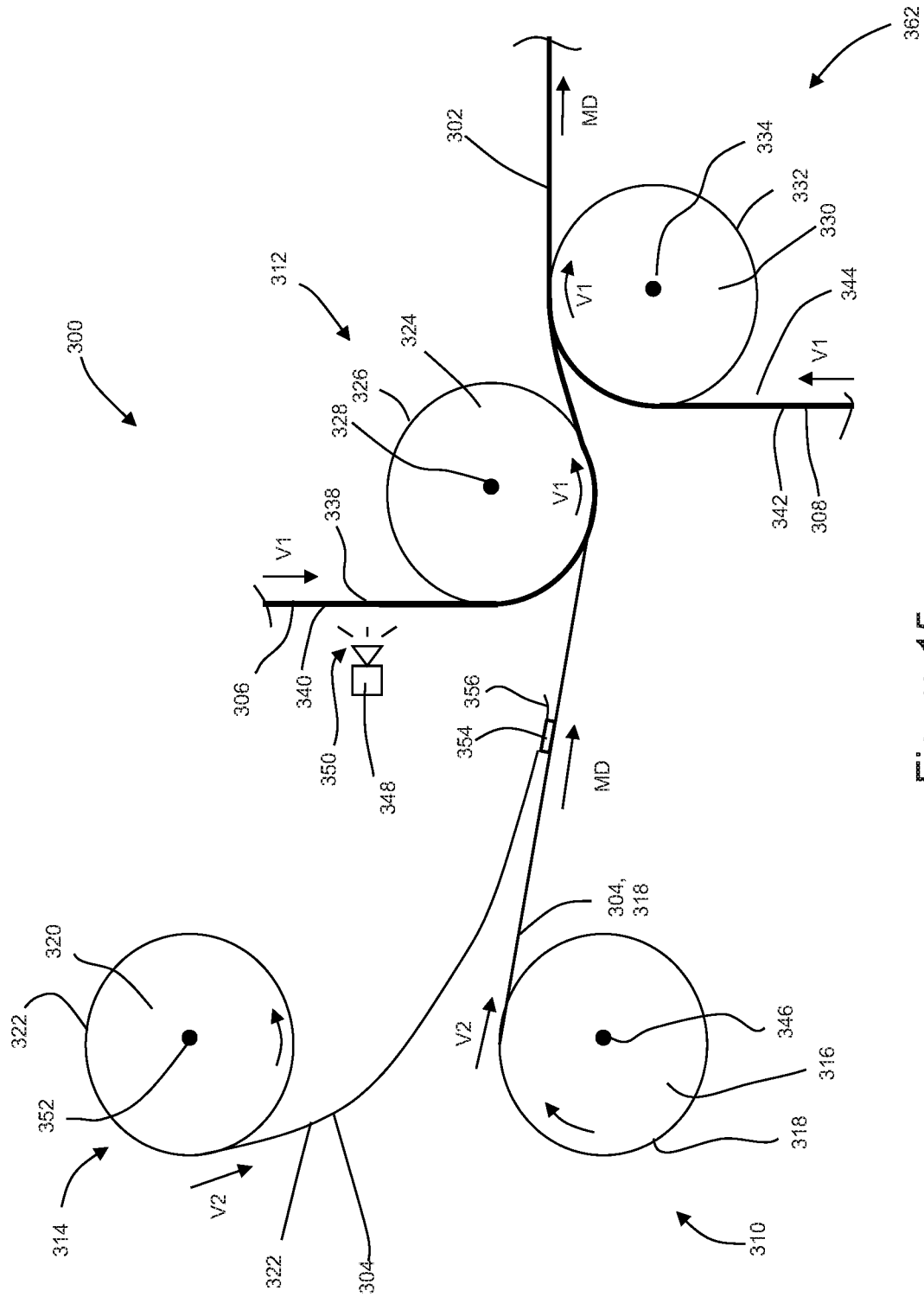
FIG. 15 is a schematic side view of the converting apparatus of FIG. 14 showing a second plurality of elastic strands connected with a first plurality of elastic strands upstream of a first roller.

As previously discussed, the apparatus 300 includes the second plurality of elastic strands 322 configured to replace the first plurality of elastic stands 318 once the first beam 316 is completely depleted or nearly depleted of first elastic strands 318. As shown in FIGS. 14 and 15, as the second beam 320 rotates, the second plurality of elastic strands 322 advance from the second beam 320 at a speed V2 with the second elastic strands 322 being spaced apart from each other in the cross direction CD. As discussed above, the second plurality of elastic strands 322 may first be connected with a splicer member 354. In turn, the splicer member 354 and the second elastic strands 322 may be connected with the first plurality of elastic strands 318 that are advancing from the first beam 316 to the first roller 324, as shown in FIG. 15. As shown in FIG. 15, the splicer member 354 and the leading ends 356 of the second plurality of elastic strands 322 advance in the machine direction MD and are positioned on the second surface 340 of the first substrate 306 on the first roller 324. From the first roller 324, the combined first substrate 306, first elastic strands 318, second elastic strands 322, and splicer member 354 advance to the second roller 330 and are positioned between the first and second substrates 306, 308. Once the second elastic strands 322 are combined with the first substrate 306 and/or second substrate 308, advancement of the first plurality of elastic strands 318 from the first beam 316 may be discontinued wherein trailing ends 358 of the first elastic strands 318 advance downstream to the first and second rollers 324, 330, such as shown in FIG. 16.

Figure 16:
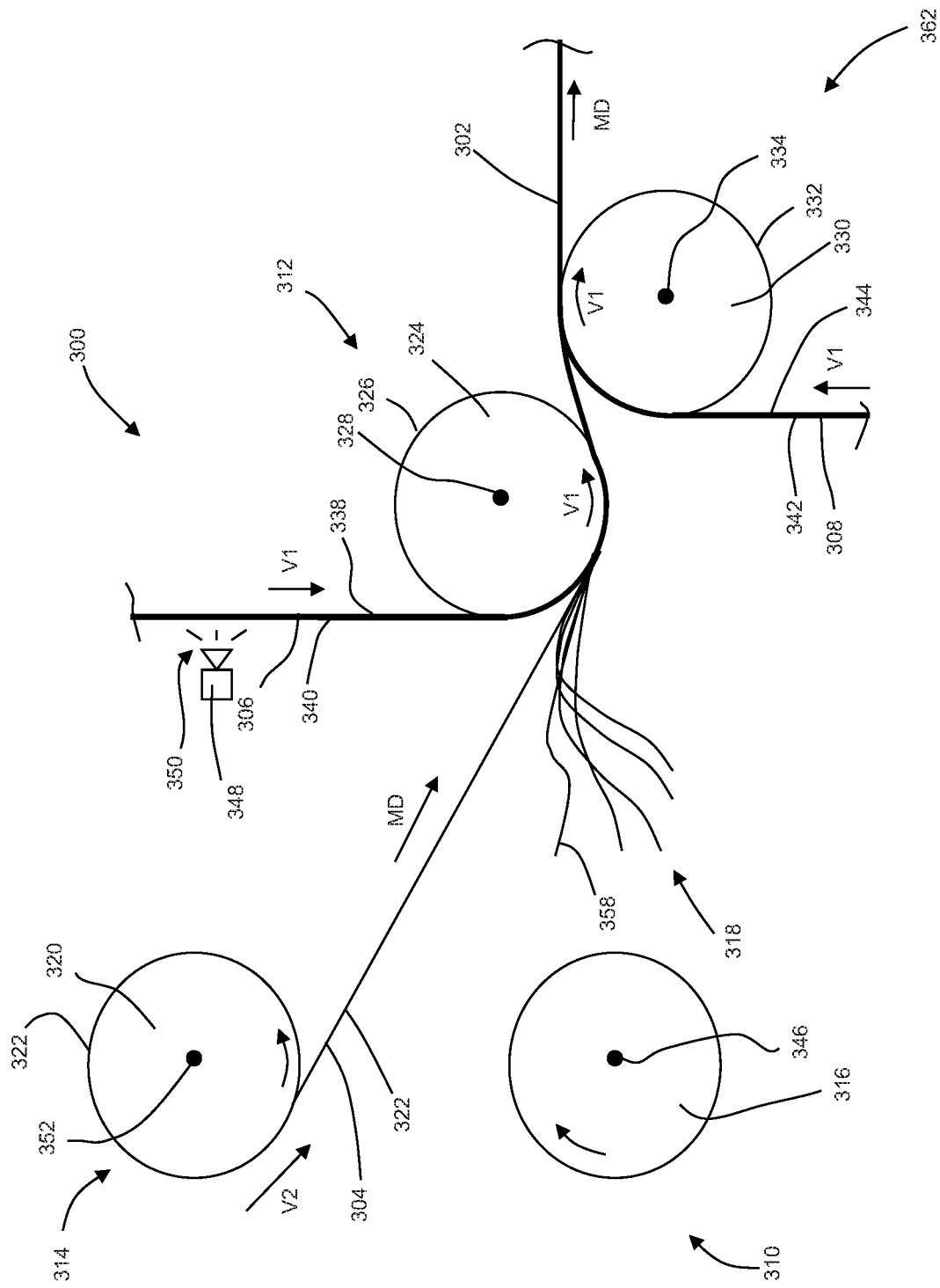
FIG. 16 is a schematic side view of the converting apparatus of FIG. 14 showing the first and second plurality of elastic strands advancing onto the first substrate.
Figure 17:
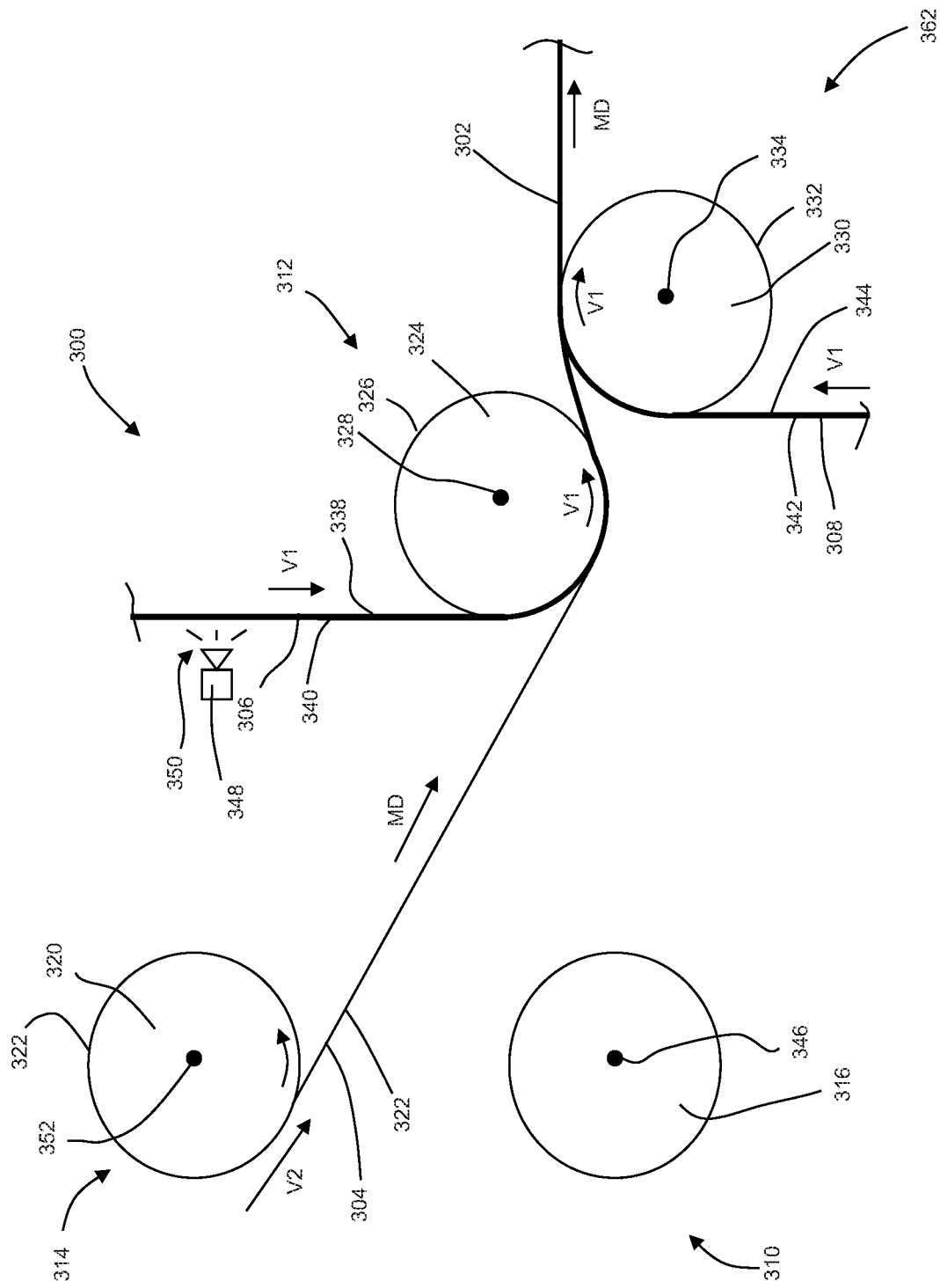
FIG. 17 is a schematic side view of the converting apparatus of FIG. 14 assembling the elastomeric laminate with the second plurality of elastic strands positioned between the first and second substrates.
Figure 18:
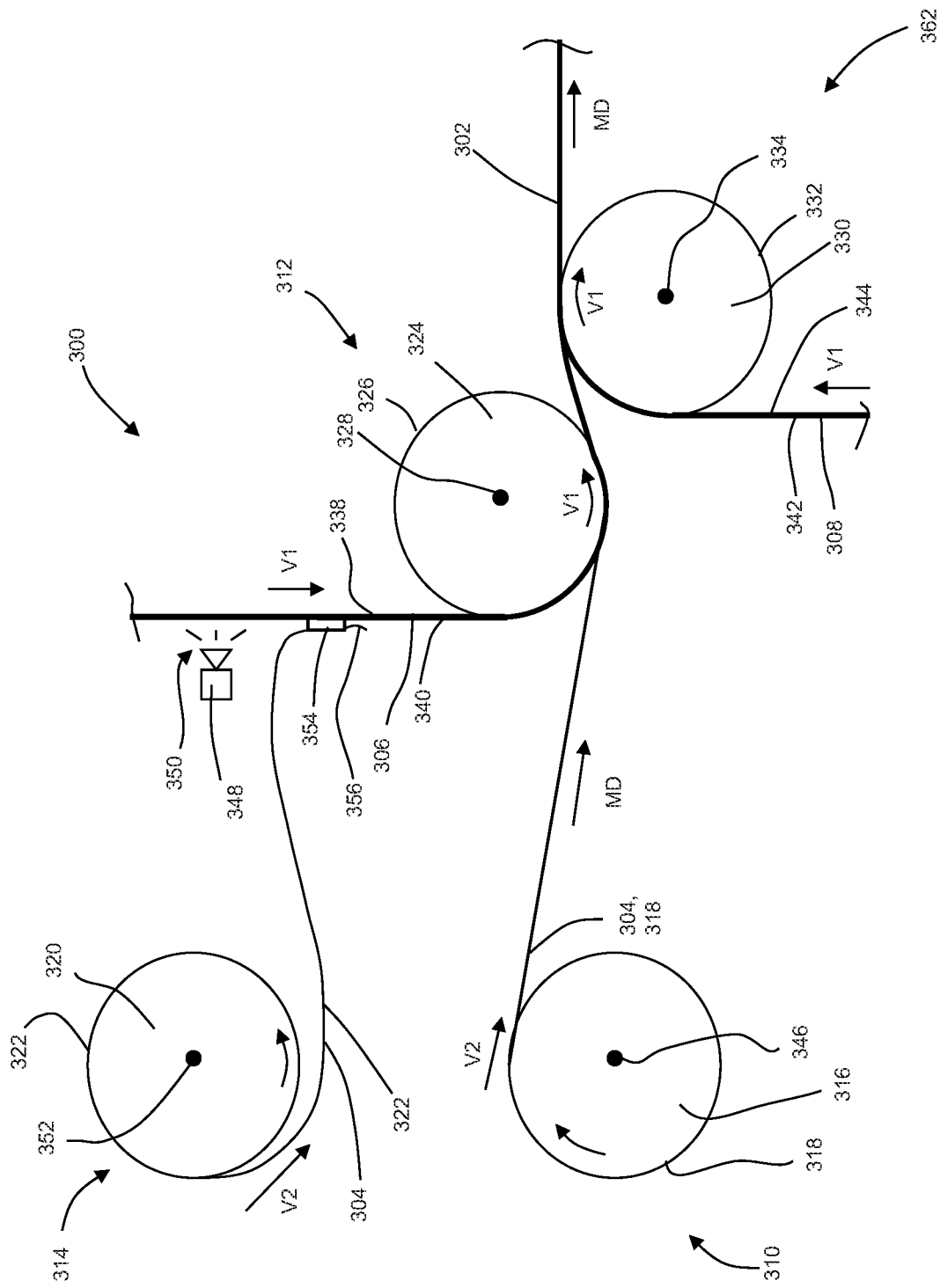
FIG. 18 is a schematic side view of the converting apparatus of FIG. 14 showing the second plurality of elastic strands connected with the first substrate upstream of the first roller.

As shown in FIGS. 16 and 17, the apparatus 300 continues to operate to assemble the elastomeric laminate 302 with the second plurality of elastic strands 322 advancing from the second beam 320. As the second beam 320 rotates, the second plurality of elastic strands 322 advance from the second beam 320 at a speed V2 with the second elastics strands 322 being spaced apart from each other in the cross direction CD. From the second beam 320, the second plurality of elastic strands 322 advances in the machine direction MD to the first roller 324 and are positioned on the second surface 340 of the first substrate 306. In some configurations, the speed V2 is less than the speed V1, and as such, the second plurality of elastic strands 322 are stretched in the machine direction MD. In turn, the stretched second elastic strands 322 advance from the first roller 324 to the second roller 330 such that the second elastic strands 322 are joined with the second surface 340 of the first substrate 306 and the first surface 342 of the second substrate 308 to produce the continuous length of elastomeric laminate 302.

As discussed above and as shown in FIG. 18, as opposed to being connected with the first elastic strands 318, the splicer member 354 and the second elastic strands 322 may be connected with the first substrate 306 upstream of the first roller 306. Once the splicer member 354 is connected with the first substrate 306, the splicer member 354 and second elastic strands 322 advance along with the first substrate 306 to the first roller 306 and the second roller 330 to assemble the elastomeric laminate 302.

As previously mentioned, the second elastic strands 322 may be introduced into the assembly operation without having to connect the second elastic strands 322 with a splicer member 354. Thus, the second elastic strands 322 may be connected directly with the first substrate 306. It is also to be appreciated that the splicer member 354 and/or the second elastic strands 322 may be connected with the first substrate 306 while partially wrapped around the outer circumferential surface 326 of the first roller 306. It is also to be appreciated that the splicer member 354 and/or the second elastic strands 322 may be connected with the second substrate 308 upstream of the second roller 330 or while partially wrapped around the outer circumferential surface 332 of the second roller 330.

Figure 19:
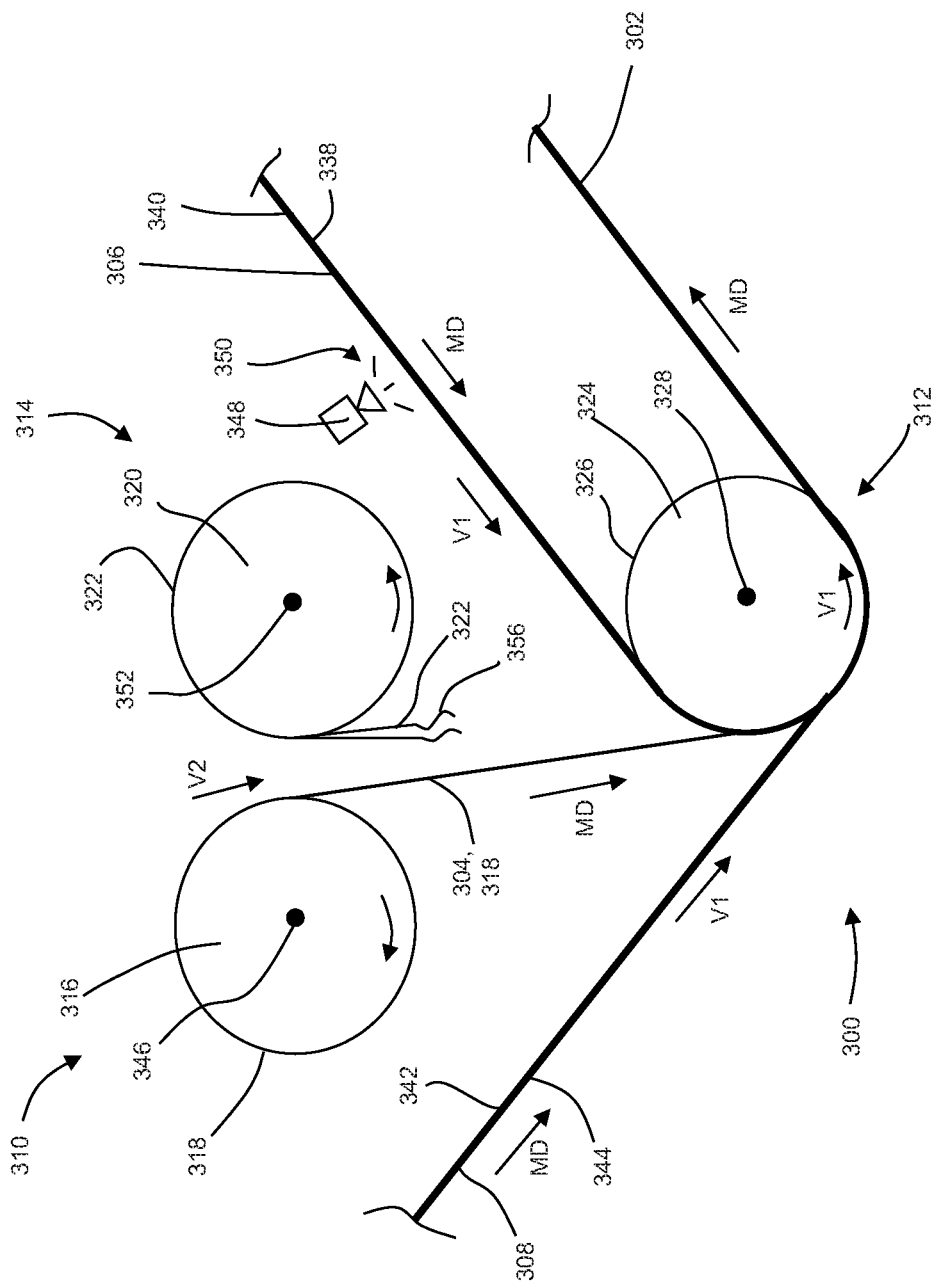
FIG. 19 is a schematic side view of a third configuration of a converting apparatus adapted to manufacture an elastomeric laminate including a first plurality of elastic strands positioned between a first substrate and a second substrate.

In a third configuration shown in FIG. 19, the apparatus 300 may be configured with only the first roller 324 and without a second roller 330. As such, the first roller 324 may be configured as the second metering device 312. As shown in FIG. 19, the first substrate 306 advances at speed V1 to the first roller 324 where the first substrate 306 partially wraps around the outer circumferential surface 326 of the first roller 324. While partially wrapped around the outer circumferential surface 326 of the first roller 324, the first substrate 306 is combined with the first elastic strands 318 and the second substrate 308. As the first beam 316 rotates, the first plurality of elastic strands 318 advance from the first beam 316 at a speed V2 with the first elastic strands 318 being spaced apart from each other in the cross direction CD. From the first beam 316, the first plurality of elastic strands 318 advances in the machine direction MD to the first roller 324 and are positioned on the second surface 340 of the first substrate 306. In some configurations, the speed V2 is less than the speed V1, and as such, the first plurality of elastic strands 318 are stretched in the machine direction MD.

With continued reference to FIG. 19, the second substrate 308 advances at speed V1 to the first roller 324 and partially wraps around the outer circumferential surface 326 of the first roller 324. In turn, the second substrate 308 is combined with the first substrate 306 and the stretched first elastic strands 318 while on the first roller 324 such that the first elastic strands 318 are joined with the second surface 340 of the first substrate 306 and the first surface 342 of the second substrate 308 to produce a continuous length of elastomeric laminate 302. As discussed above, the first substrate 306 may advance past an adhesive applicator device 348 that applies adhesive 350 to the second surface 340 of the first substrate 306 while advancing to the first roller 324. It is to be appreciated that the adhesive 350 may be applied to the first substrate 306 while the first substrate 306 is partially wrapped around the outer circumferential surface 326 of the first roller 324. It is to be appreciated that adhesive may also be applied to the first elastic strands 318 before and/or while being joined with first substrate 306 and second substrate 308. In addition, it is to be appreciated that adhesive may be applied to the first surface 342 of the second substrate 308 before or while being joined with the first elastic strands 318 and first substrate 306.

Figure 20:
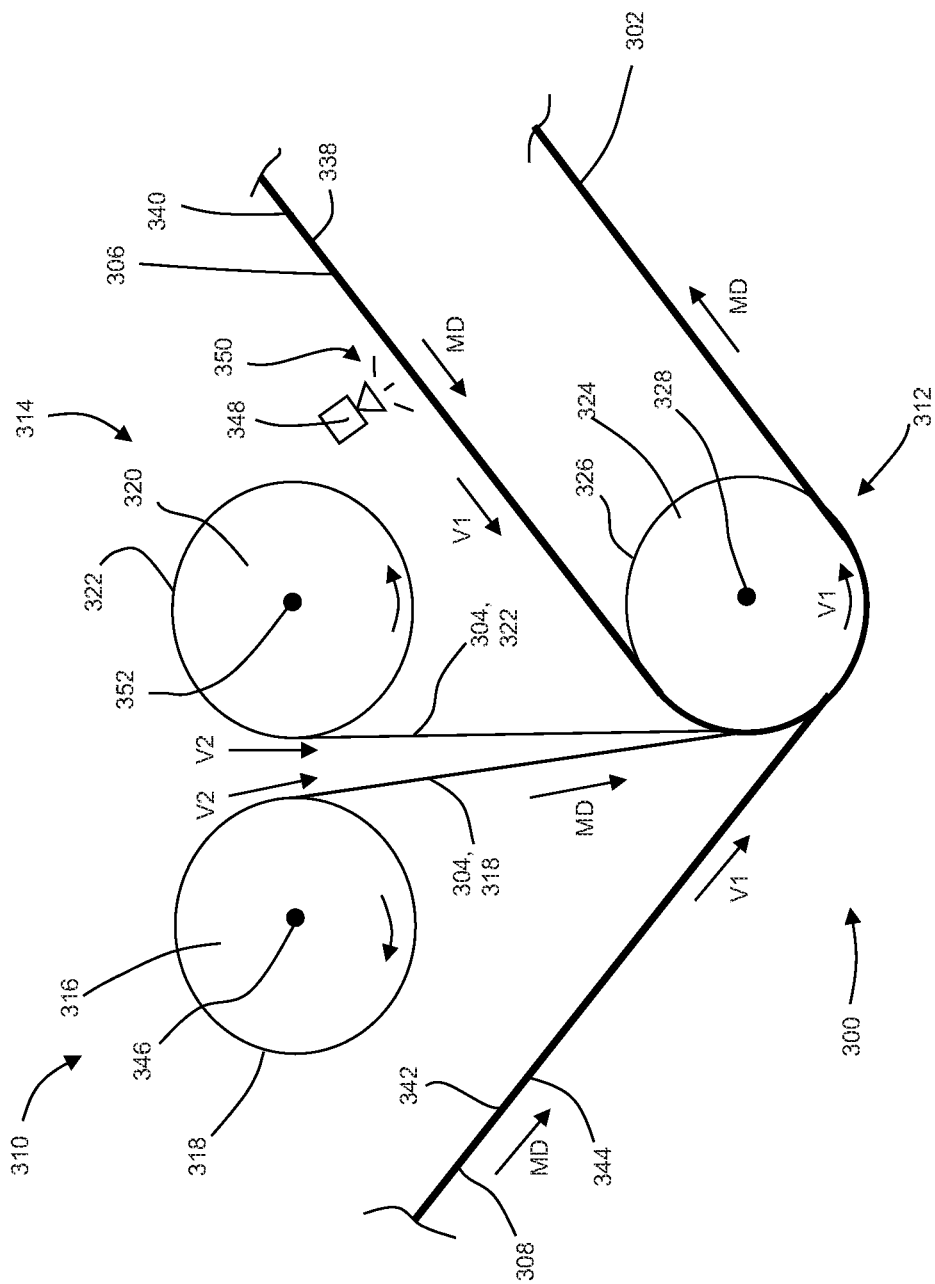
FIG. 20 is a schematic side view of the converting apparatus of FIG. 19 assembling the elastomeric laminate with the first and second plurality of elastic strands advancing between the first and second substrates.

As previously discussed, the apparatus 300 includes the second plurality of elastic strands 322 configured to replace the first plurality of elastic stands 318 once the first beam 316 is completely depleted or nearly depleted of first elastic strands 318. As shown in FIGS. 19 and 20, as the second beam 320 rotates, the second plurality of elastic strands 322 advance from the second beam 320 at a speed V2 with the second elastic strands 322 being spaced apart from each other in the cross direction CD. In turn, leading ends 356 of the second plurality of elastic strands 322 may be advanced onto the first roller 324 and between first substrate 306 and the second substrate 308. As such, the second plurality of elastic strands 322 are positioned in between the second surface 340 of the first substrate 306 and the first surface 342 of the second substrate 308 such that the first plurality of elastic strands 318, the second plurality of elastic strands 322, and the first substrate 306 are positioned between the second substrate 308 and the outer circumferential surface 326 of the first roller 324. As discussed above, the second plurality of elastic strands 322 may also be first connected with a splicer member 354. Thus, it is to be appreciated that the splicer member 354 and/or the second elastic strands 322 may be connected with the first plurality of elastic strands 318, the first substrate 306, or second substrate 308. As shown in FIGS. 19 and 20, the leading ends 356 of the second plurality of elastic strands 322 advance in the machine direction MD and are positioned on the second surface 340 of the first substrate 306 on the first roller 324. And the second substrate 306 advances to the first roller 324 to be combined with first substrate 306, first elastic strands 318, and second elastic strands 322 to form the elastomeric laminate 302. Once the second elastic strands 322 are combined with the first substrate 306 and/or second substrate 308, advancement of the first plurality of elastic strands 318 from the first beam 316 may be discontinued wherein trailing ends 358 of the first elastic strands 318 advance downstream to the first roller 324, such as shown in FIG. 21.

Figure 21:
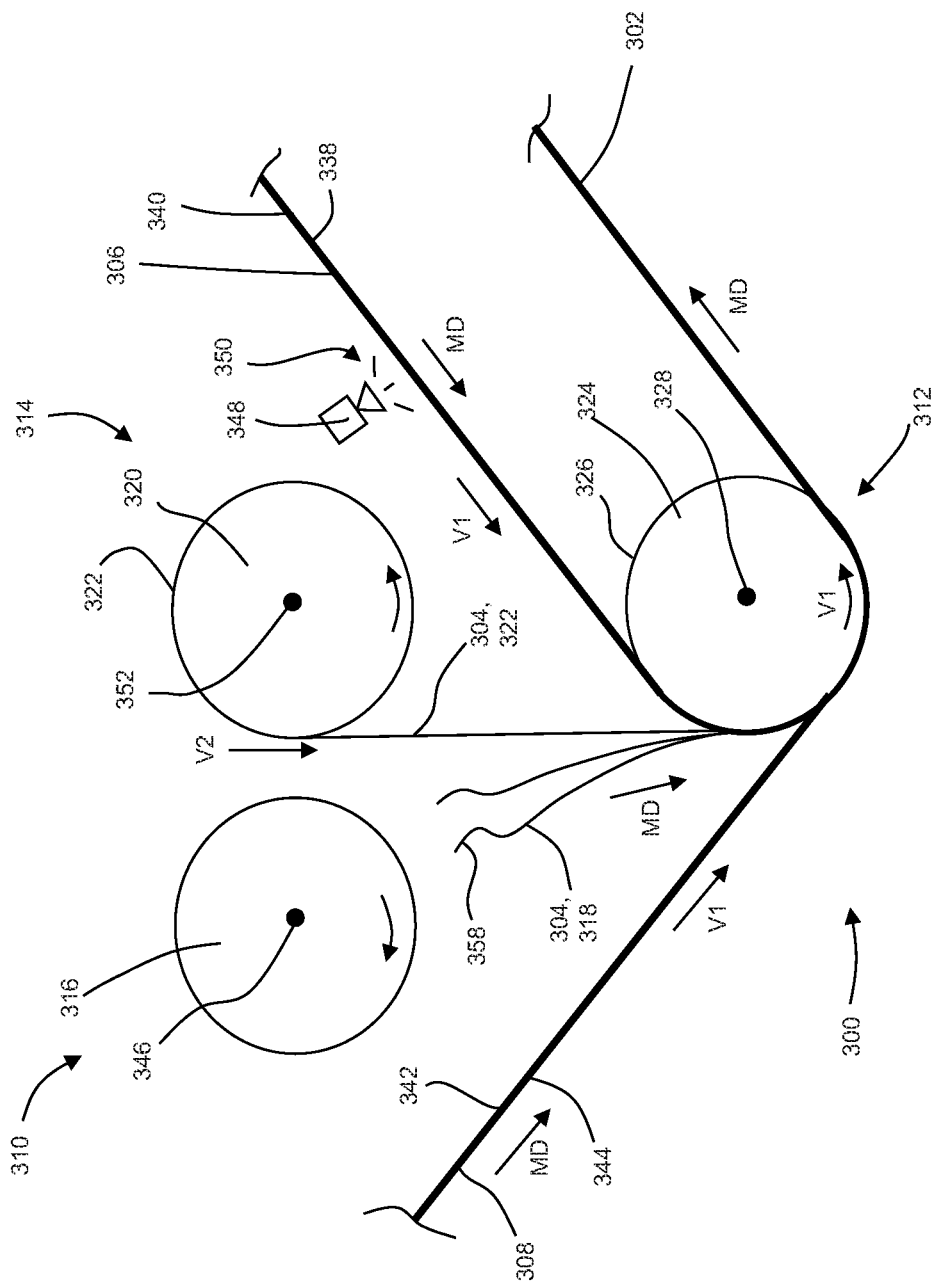
FIG. 21 is a schematic side view of the converting apparatus of FIG. 19 assembling the elastomeric laminate showing the trailing ends of the first plurality of elastic strands advancing between the first and second substrates.
Figure 22:
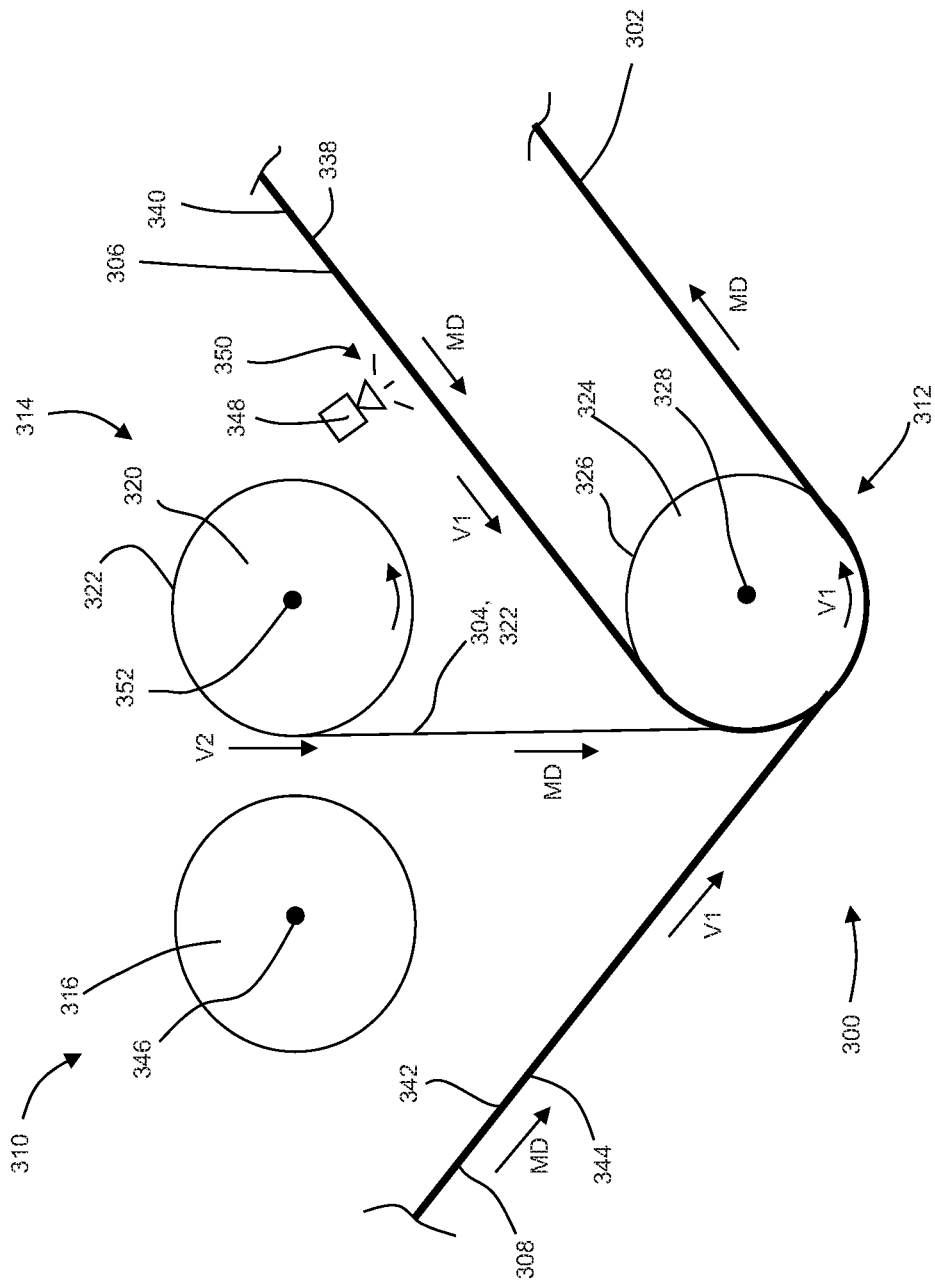
FIG. 22 is a schematic side view of the converting apparatus of FIG. 19 assembling the elastomeric laminate with the second plurality of elastic strands positioned between the first and second substrates.

As shown in FIGS. 21 and 22, the apparatus 300 continues to operate to assemble the elastomeric laminate 302 with the second plurality of elastics 322 advancing from the second beam 320. As the second beam 320 rotates, the second plurality of elastic strands 322 advance from the second beam 320 at a speed V2 with the second elastic strands 322 being spaced apart from each other in the cross direction CD. From the second beam 320, the second plurality of elastic strands 322 advances in the machine direction MD to the first roller 324 and are positioned on the second surface 340 of the first substrate 306. In some configurations, the speed V2 is less than the speed V1, and as such, the second plurality of elastic strands 322 are stretched in the machine direction MD. In turn, the stretched second elastic strands 322 are joined with the second surface 340 of the first substrate 306 and the first surface 342 of the second substrate 308 to produce the continuous length of elastomeric laminate 302 that advances from the first roller 324.

It is to be appreciated that in the various process configurations discussed above, the second plurality of elastic strands 322 may be first connected with a splicer member 354 before advancing the elastic strands 322 in the assembly process. It is also to be appreciated that in the various process configurations discussed above, the second plurality of elastic strands 322 may be advanced directly into the assembly process without connecting the stands 322 to a splicer member. In some configurations, the second plurality of elastic strands 322 may be connected or tied to each other with a knot before advancing into the assembly process. In some configurations, the first and/or second substrate may have an electrostatic charge that attracts the strands 322 to the substrates before advancing into assembly process. Further, in some configurations, strands 322 may be directed into the assembly process by air flow, such as provided from a fan and/or a vacuum system.

Figure 23:
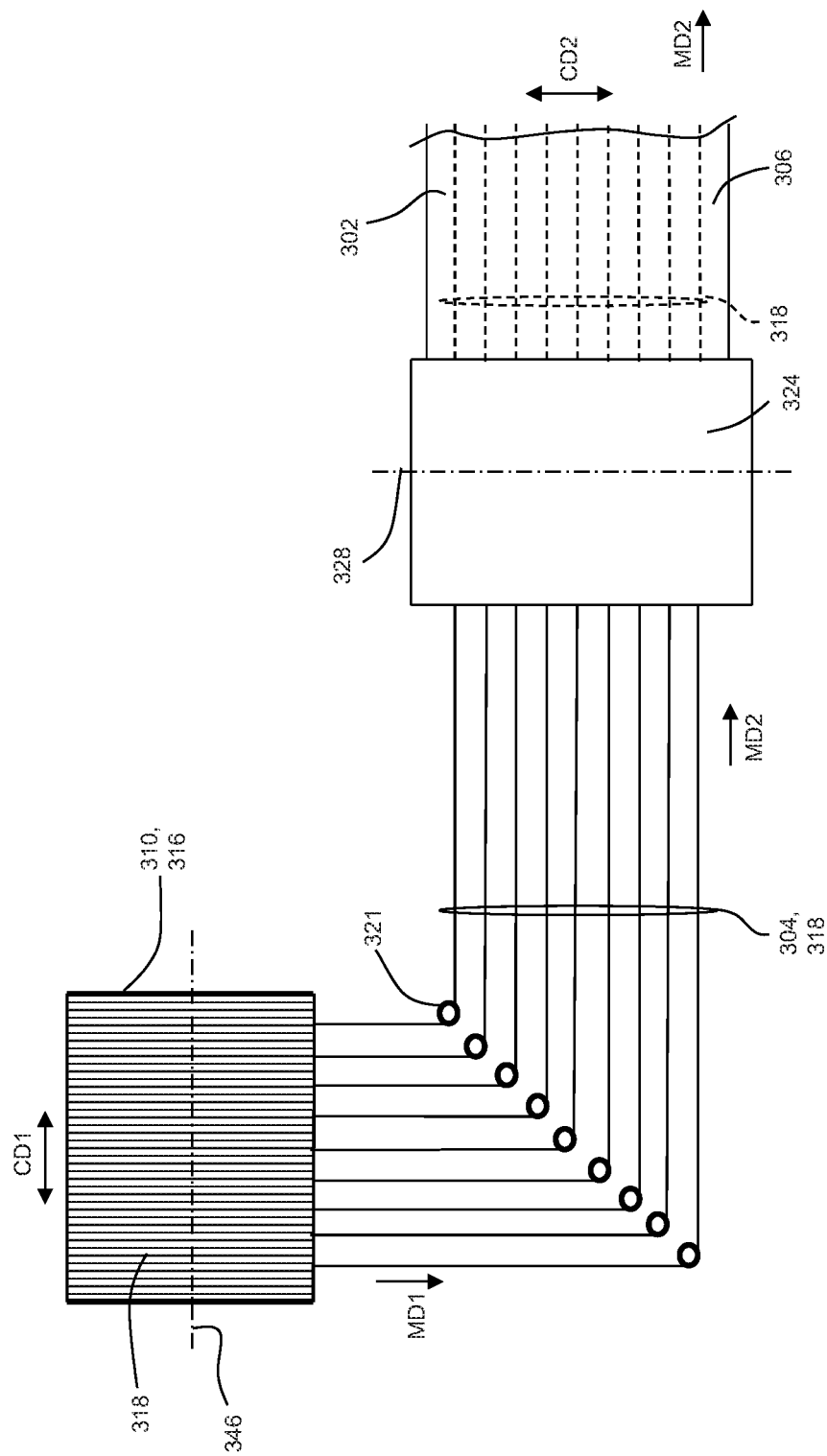
FIG. 23 is a schematic side view of a converting apparatus adapted to manufacture an elastomeric laminate.

As illustrated herein, the apparatuses and processes may be configured such that elastic strands may be advanced from the beams and directly to the assembly process without having to touch additional machine components, such as for example, guide rollers. It is also to be appreciated that in some configurations, elastic strands may be advanced from the beams and may be redirected and/or otherwise touched by and/or redirected before advancing to the assembly process. For example, FIG. 23 shows a configuration where the first beam rotation axis 346 may extend in a first cross direction CD1. As the first beam 316 rotates, the first plurality of elastic strands 318 advance from the first beam 316 in a first machine direction MD1 with the first elastic strands 318 being spaced apart from each other in the first cross direction CD1. The elastic strands 318 may then be redirected by rollers 321 from the first machine direction MD1 to a second machine direction MD2, wherein the elastic strands 318 may remain separated from each other in a second cross direction CD2. From the rollers 321, the elastic strands 318 may advance in the second machine direction MD2 to be combined with the first and second substrates 306, 308 to form the elastic laminate 302. Thus, it is to be appreciated that the first and/or second beams 316, 320 may be arranged and/or oriented such that the beam rotation axis 346, 352 may be parallel, perpendicular, or otherwise angularly offset with respect to the machine direction advancement of the elastic laminate 302 and/or the substrates 306, 308.

It is to be appreciated that a control system and/or an inspection system may be utilized to control various aspects of the splicing operations discussed herein. For example, as previously mentioned, the first beam 316 and the second beam 320 may be connected with one or more motors, such as servo motors, to drive and control the rotation of the beams 316, 320. As such, a control system may operate to control the acceleration and/or deceleration of the first and/or second beams 316, 320 during the splicing operation to achieve and/or maintain the desired tension in the elastic strands. In some configurations, the elastic strands may be advanced from the beams 316, 320 through a series of dancer rolls to help maintain desired tensions in the elastic strands during splicing operations. As previously mentioned, the elastomeric laminate 302 may also be subject to additional converting processes. Such additional converting processes may incorporate the elastomeric laminate 302 into discrete absorbent articles 100. As such, in some embodiments, an inspection system may be configured to detect and/or track a defective length of the elastomeric laminate 302. With reference to FIG. 9, a defective length of elastomeric laminate 302 may be defined by a length of elastomeric laminate 302 that includes both the first elastic strands 318 and the second elastic strands 322 positioned together between the first and second substrates 306, 308. A defective length of elastomeric laminate 302 may also be defined by a length of elastomeric laminate 302 that includes the splicer member 354, leading ends 356 of the second elastic strands 322, and/or the trailing ends 358 of the first elastic strands 318. The inspection system may also correlate inspection results and measurements from the defect length of the elastomeric laminate 302 with absorbent articles 100 made therefrom. In turn, the inspection system may be used to control a reject system on a converting process of absorbent articles, wherein absorbent articles manufactured with portions of the defective length of elastomeric laminate 302 are rejected. In some configurations, defective articles may be subject to the rejection system and removed from the assembly process. Absorbent articles 100 that are not deemed to be defective may be subject to further processing steps, such as folding and packaging. In some configurations, an inspection system may be configured to detect a broken elastic strand advancing from a first beam 316. Upon detection of a broken elastic strand, the inspection system may activate a splicing operation, such as described above, to place a second beam 320 into service and remove the first beam 316 from service. In some configurations, an inspection and/or a control system may operate to control the timing and placement of the splicer member 354 into the assembly operation, such as in the nip 336 shown in FIG. 4, which may help an inspection system to more accurately track a splicing event. It is to be appreciated that such an inspection system may be configured in various ways, such as disclosed in U.S. Patent Publication No. 2013/0199696 A1.

This application claims the benefit of U.S. Provisional Application No. 62/436,589, filed on Dec. 20, 2016; 62/483,965, filed on Apr. 11, 2017; 62/553,538, filed on Sep. 1, 2017; 62/553,149, filed on Sep. 1, 2017; 62/553,171, filed on Sep. 1, 2017; and 62/581,278, filed on Nov. 3, 2017, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an elastomeric laminate, the method comprising steps of:
providing a first plurality of elastic strands wound onto a first beam;
providing a second plurality of elastic strands wound onto a second beam;
rotating a first roller about a first axis of rotation extending in a cross direction, the first roller comprising an outer circumferential surface comprising a surface speed V1;
rotating a second roller about a second axis of rotation extending in the cross direction, the second roller comprising an outer circumferential surface comprising a surface speed V1, wherein the first roller and the second roller rotate in opposite directions, and wherein the first roller is adjacent the second roller to define a nip between the first roller and the second roller;
advancing a first substrate and a second substrate through the nip;
rotating the first beam to unwind the first plurality of elastic strands from the first beam in a machine direction at a speed V2, wherein the first plurality of elastic strands are separated from each other in the cross direction, and wherein V2 is less than V1;
stretching the first plurality of elastic strands in the machine direction by advancing the first plurality of elastic strands from the first beam through the nip and between the first substrate and the second substrate;
connecting the second plurality of elastic strands with a splicer member;
rotating the second beam to unwind the second plurality of elastic strands from the second beam in the machine direction, wherein the second plurality of elastic strands are separated from each other in the cross direction;
advancing the splicer member and the second plurality of elastic strands through the nip;
connecting the splicer member with the first substrate subsequent to the step of connecting the second plurality of elastic strands with the splicer member and prior to the step of advancing the splicer member through the nip; and
discontinuing advancement of the first plurality of elastic strands through the nip subsequent to advancing the splicer member through the nip.

2. The method of claim 1, wherein the splicer member comprises a tacky surface and wherein the step of connecting the second plurality of elastic strands with the splicer member further comprises adhering the tacky surface with the second plurality of elastic strands.

3. The method of claim 1, further comprising a step of bonding the first substrate together with the second substrate.

4. The method of claim 1, further comprising a step of: applying adhesive to the first substrate.

5. The method of claim 1, further comprising a step of applying adhesive to the first plurality of elastic strands.

6. The method of claim 1, further comprising a step of stretching the second plurality of elastic strands in the machine direction by advancing the second plurality of elastic strands from the second beam through the nip between the first substrate and the second substrate.

7. The method of claim 1, wherein the first plurality of elastic strands comprises at least 50 elastic strands.

8. The method of claim 1, wherein the first plurality of elastic strands comprises a decitex of less than 1000.

9. A method for making an elastomeric laminate, the method comprising steps of:
providing a first plurality of elastic strands wound onto a first beam;
providing a second plurality of elastic strands wound onto a second beam;
rotating a first roller about a first axis of rotation extending in a cross direction, the first roller comprising an outer circumferential surface comprising a surface speed V1;
providing a first substrate comprising a first surface and an opposing second surface;
advancing the first surface of the first substrate onto the outer circumferential surface of the first roller;
rotating the first beam to unwind the first plurality of elastic strands from the first beam in a machine direction at a speed V2, wherein the first plurality of elastic strands are separated from each other in the cross direction, and wherein V2 is less than V1;
stretching the first plurality of elastic strands in the machine direction by advancing the first plurality of elastic strands from the first beam onto second surface of the first substrate;
advancing the combined first substrate and the first plurality of elastic strands in the machine direction from the first roller;
connecting the second plurality of elastic strands with a splicer member;
rotating the second beam to unwind the second plurality of elastic strands from the second beam in the machine direction, wherein the second plurality of elastic strands are separated from each other in the cross direction;

combining the splicer member and the second plurality of elastic strands with the first plurality of elastic strands on the second surface of the first substrate;

connecting the splicer member with the first substrate subsequent to the step of connecting the second plurality of elastic strands with the splicer member; and subsequently discontinuing advancement of the first plurality of elastic strands onto the second surface of the first substrate.

10. The method of claim 9, further comprising steps of:
providing a second substrate comprising a first surface and an opposing second surface; and
positioning the first surface of the second substrate in a facing relationship with the second surface of the first substrate with the first plurality of elastic strands between the first substrate and the second substrate.

11. The method of claim 10, further comprising steps of:
rotating a second roller about a second axis of rotation extending in the cross direction, the second roller comprising an outer circumferential surface comprising a surface speed V1; and
advancing the first surface of the second substrate onto the outer circumferential surface of the second roller.

12. The method of claim 9, wherein the splicer member comprises a tacky surface and wherein the step of connecting the second plurality of elastic strands with the splicer member further comprises adhering the tacky surface with the second plurality of elastic strands.

13. A method for making an elastomeric laminate, the method comprising steps of:
providing a first plurality of elastic strands wound onto a first beam;
providing a second plurality of elastic strands wound onto a second beam;
rotating a roller about a first axis of rotation extending in a cross direction, the roller comprising an outer circumferential surface;
providing a first substrate and a second substrate, each comprising a first surface and an opposing second surface;
advancing the first surface of the first substrate onto the outer circumferential surface of the roller;
rotating the first beam to unwind the first plurality of elastic strands from the first beam in a machine direction, wherein the first plurality of elastic strands are separated from each other in the cross direction;
stretching the first plurality of elastic strands in the machine direction while advancing the first plurality of elastic strands from the first beam onto the second surface of the first substrate;
advancing the first surface of the second substrate onto the second surface of the first substrate such that the first plurality of elastic strands and the first substrate are positioned between the second substrate and the outer circumferential surface of the roller;
advancing the combined first substrate, second substrate, and the first plurality of elastic strands in the machine direction from the roller;
rotating the second beam to unwind the second plurality of elastic strands from the second beam in the machine direction, wherein the second plurality of elastic strands are separated from each other in the cross direction;
advancing the second plurality of elastic strands in between the second surface of the first substrate and the first surface of the second substrate such that the first plurality of elastic strands, the second plurality of elastic strands, and the first substrate are positioned between the second substrate and the outer circumferential surface of the roller;
connecting the second plurality of elastic strands with a splicer member;
connecting the splicer member with the first substrate subsequent to the step of connecting the second plurality of elastic strands with the splicer member; and
subsequently discontinuing advancement of the first plurality of elastic strands onto the second surface of the first substrate.

14. The method of claim 13, further comprising a step of: applying adhesive to the first substrate.

* * * * *